(12) United States Patent
Fan et al.

(10) Patent No.: US 7,741,340 B2
(45) Date of Patent: Jun. 22, 2010

(54) HYDROXY PIPERIDINE DERIVATIVES TO TREAT GAUCHER DISEASE

(75) Inventors: Jian-Qiang Fan, Demarest, NJ (US); Xiaoxiang Zhu, North Brunswick, NJ (US); Kamlesh Sheth, North Brunswick, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 774 days.

(21) Appl. No.: 10/988,428

(22) Filed: Nov. 12, 2004

(65) Prior Publication Data

US 2005/0130972 A1 Jun. 16, 2005

Related U.S. Application Data

(60) Provisional application No. 60/519,496, filed on Nov. 12, 2003.

(51) Int. Cl.
*A61K 31/445* (2006.01)
(52) U.S. Cl. .................. 514/315; 514/328; 546/242
(58) Field of Classification Search .............. 514/317, 514/315, 328; 546/242
See application file for complete search history.

(56) References Cited

U.S. PATENT DOCUMENTS

| | | | |
|---|---|---|---|
| 5,051,407 A | 9/1991 | Boshagen et al. | |
| 5,580,757 A | 12/1996 | Desnick et al. | |
| 5,658,567 A | 8/1997 | Calhoun et al. | |
| 6,066,626 A | 5/2000 | Yew et al. | |
| 6,083,725 A | 7/2000 | Selden et al. | |
| 6,274,597 B1 | 8/2001 | Fan et al. | |
| 6,335,011 B1 | 1/2002 | Podsakoff et al. | |
| 6,583,158 B1 | 6/2003 | Fan et al. | |
| 6,589,964 B2 | 7/2003 | Fan et al. | |
| 6,599,919 B2 | 7/2003 | Fan et al. | |
| 6,696,059 B2 | 2/2004 | Jacob et al. | |
| 6,916,829 B2* | 7/2005 | Fan et al. | 514/315 |
| 7,141,582 B2* | 11/2006 | Fan et al. | 514/315 |
| 2007/0021381 A1* | 1/2007 | Fan et al. | 514/62 |

FOREIGN PATENT DOCUMENTS

WO WO2004/037373 5/2004

OTHER PUBLICATIONS

Zhu et. al. Angewandte Chemie International Edition English 2005, 44, 7450-7453.*
Marina Jmoudiak and Anthony H. Futerman "Gaucher disease: pathological mechanisms and modern management" British Journal of Haematology, 2005, 129, 178-188.*
U.S. National Library of Medicine Genetics Home Reference "GBA" online "http://ghr.nlm.nih.gov/gene=gba" Jun. 18, 2007.*
A. R. Sawkar, W. D'Haeze and J. W. Kelly "Human Genome & Diseases: Review Therapeutic strategies to ameliorate lysosomal storage disorders—a focus on Gaucher disease" Cellular and Molecular Life Sciences 2006, 63, 1179-1192.*
Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Asano, Naoki, et al. 2000. In vitro inhibition and intracellular enhancement of lysosomal α-galactosidase A activity in Fabry lymphoblasts by 1-by 1-deoxygalactonojiuimycin and its derivatives. *Eur. J. Biochem.* 267:4179-4186.
Best, Wayne M., et al. 2002. The synthesis of a carbohydrate-like dihydrooxazine and tetrahydrooxazine as putative inhibitors of glycoside hydrolases: A direct synthesis of isofagomine. *Can. J. Chem.* 80:857-865.
Bishop, David F., et al. 1986. Human α-galactosidase A: Nucleotide sequence of a cDNA clone encoding the mature enzyme. *Proc. Natl. Acad. Sci. USA* 88:4859-4863.
Brady, Roscoe O., et al., 1965. Metabolism of Glucocerebrosides—II. Evidence of an Enzymatic Deficiency in Gaucher's Disease. *Biochemical and Biophysical Research Communications* 18(2):221-225.
Burrows, Jon A.J., et al. 2000. Chemical chaperones mediate increased secretion of mutant α1-antitrypsin (α1-AT) Z: A potential pharmacological strategy for prevention of livery injury and empnhysema in α1-AT deficiency. *Proc. Natl. Acad. Sci. USA* 97(4):1796-1801.
Butters, Terry D., et al. 2003. Small-molecule therapeutics for the treatment of glycolipid lysosomal storage disorders. *Phil. Trans R. Soc. Lond.* 358:927-945.
Cox, Timothy, et al. 2000. Novel oral treatment of Gaucher's disease with N-butyldeoxynojirimycin (OGT 918) to decrease substrate biosynthesis. *The Lancet* 355:1481-1485.
Dvir, Hay, et al. 2003. X-ray structure of human acid-β-glucosidase, the defective enzyme in Gaucher disease. *EMBO reports* 4(7):1-6.
Fan, Jian-Qiang, et al. 1999. Accelerated transport and maturation of lysosomal α -galactosidase A in Fabry lymphoblasts by an enzyme inhibitor. *Nature Medicine* 5(1)112-115.

(Continued)

*Primary Examiner*—Rita J Desai
*Assistant Examiner*—David K O'Dell
(74) *Attorney, Agent, or Firm*—Hoffmann & Baron, LLP

(57) ABSTRACT

The present invention provides novel hydroxy piperidine (HP) derivatives having (i) a positive charge at the position corresponding to the anomeric position of a pyranose ring; (ii) a short, flexible linker emanating from the corresponding position of the ring oxygen in a pyranose; and (iii) a lipophilic moiety connected to the linker and pharmaceutically acceptable salts thereof. The linker can be absent if the lipophilic moiety corresponds to a hydrocarbon chain with a linear length of 6 or more carbons. The present invention further provides a method for treating individuals having Gaucher disease by administering the novel HP derivative as "active-site specific chaperones" for the mutant glucocerebrosidase associated with the disease.

6 Claims, 5 Drawing Sheets

OTHER PUBLICATIONS

Greenberg, Paul, et al. 1990. Human acid β-glucosidase: use of sphingosyl and N-alkyl-glucosylamine inhibitors to investigate the properties of the active site. *Biochimica et Biophysica Acta* 1039:12-20.

Heightman, Tom D., and Vasella, Andrea T. 1999. Recent Insights into Inhibition, Structure, and Mechanism of Configuration-Retaining Glycosidases. *Angew. Chem. Int. Ed.* 38:750-770.

Ichikawa, Yoshitaka, et al. 1998. 1-N-Iminosugars: Potent and Selective Inhibitors of β-Glycosidases. *J. Am. Chem. Soc.* 120:3007-3018.

Inokuchi, Jin-ichi, and Radin, Norman S. 1987. Preparation of the active isomer of 1-phenyl-2-decanoylamino-3-morpholino-1-propanol, inhibitor of murine glucocerebroside synthetase. *Journal of Lipid Research* 28:565-571.

Ishii, Satoshi, et al. 1993. Characterization of a Mutant α-Galactosidase Gene Product for the Late-Onset Cardiac Form of Fabry Disease. *Biochemical and Biophysical Research Communications* 197(3):1585-1589.

Kim, Yong Jip, et al. 2000. Highly Selective Synthesis of 1-N-Iminosugars of the D-Glucose and -Glucuronic Acid Types. *J. Org. Chem.* 65:2599-2602.

Kohmura, Yoshinori, and Mase, Toshiaki. 2004. A Highly Stereoselective Synthesis of Optically Active Trisubstituted 1,2-Ethylenediamines: The First Example of Grignard Addition to N-Diphenylphosphinoyl Ketimines Derived from Amino Acids. *J. Org. Chem.* 69:6329-6334.

Lillelund, Vinni H., et al. 2002. Recent Developments of Transition-State Analogue Glycosidase Inhibitors of Non-Natural Product Origin. *Chem. Rev.* 102:515-553.

Ogawa, Seiichiro, et al. 1996. Synthesis of Potent β-D-Glucocerebrosidase Inhibitors: N-Alkyl-β-Valienamines. *Bioorganic & Medicinal Chemistry Letters* 6(8):929-932.

Platt, Frances M., et al. N-Butyldeoxygalactonojirimycin Inhibits Glycolipid Biosynthesis but Does Not Affect N-Linked Oligosaccharide Processing. *The Journal of Biological Chemistry* 269(43):27108-27114.

Platt, Frances M., and Butters, Terry D. 1998. New Therapeutic Prospects for the Glycosphingolipid Lysosomal Storage Diseases. *Biochemical Pharmacology* 56:421-430.

Sawkar, Anu R., et al. 2002. Chemical chaperones increase the cellular activity of N370S β-glucosidase: A therapeutic strategy for Gaucher Disease. *Proc. Natl. Aced. Sci. USA* 99(24):15428-15433.

Sawkar et al., "Chemical chaperones increase the cellular activity of N370S b-glucosidase: A therapeutic strategy for Gaucher disease," PNAS, Nov. 26, 2002, vol. 99, No. 24, 15428-15433.

Priestman et al., "Imino sugar therapy for type 1 Gaucher disease," Glycobiology. 2000; 11: iv-vi.

Panday et al., Very Strong Inhibition of Glucosidases by C(2)-Substituted Tetrahydroimidazopyridines, Helvetica Chimica Acta. 2000; 83: 58-79.

Plesner et al., Accurate Determination of Rate Constants of Very Slow, Tight-Binding Competitive Inhibitors by Numerical Solution of Differential Equations, Independently of Precise Knowledge of the Enzyme Concentration; Analytical Biochemistry. 2001; 295: 186-193.

Ruvinov et al., Monovalent Cations Partially Repair a Conformational Defect in a Mutant Tryptophan Synthase α2β2 Complex (β-E109A)*; J. Biol. Chem. 1995; 270: 17333-38.

* cited by examiner

HYDROXY PIPERIDINE DERIVATIVES TO TREAT GAUCHER DISEASE

This application claims priority to provisional application 60/519,496 filed Nov. 12, 2003, herein incorporated by reference.

FIELD OF THE INVENTION

The present invention provides novel hydroxy piperidine (HP) derivatives having (i) a positive charge at the position corresponding to the anomeric position of a pyranose ring; (ii) a short, flexible linker emanating from the corresponding position of the ring oxygen in a pyranose; and (iii) a lipophilic moiety connected to the linker and pharmaceutically acceptable salts thereof. Alternatively the linker can be absent if the lipophilic moiety corresponds to a hydrocarbon chain with a linear length of 6 or more carbons. The present invention further provides a method for treating individuals having Gaucher disease by administering the novel HP derivative as "active-site specific chaperones" for the mutant glucocerebrosidase associated with the disease.

BACKGROUND OF THE INVENTION

Protein Folding

Proteins are synthesized in the cytoplasm, and the newly synthesized proteins are secreted into the lumen of the endoplasmic reticulum (ER) in a largely unfolded state. In general, protein folding is governed by the principle of self assembly. Newly synthesized polypeptides fold into their native conformation based on their amino acid sequences (Anfinsen et al., *Adv. Protein Chem.* 1975; 29:205-300). In vivo, protein folding is complicated, because the combination of ambient temperature and high protein concentration stimulates the process of aggregation, in which amino acids normally buried in the hydrophobic core interact with their neighbors non-specifically. To avoid this problem, protein folding is usually facilitated by a special group of proteins called molecular chaperones which prevent nascent polypeptide chains from aggregating, and bind to unfolded protein such that the protein refolds in the native conformation (Hartl, *Nature* 1996; 381:571-580).

Molecular chaperones are present in virtually all types of cells and in most cellular compartments. Some are involved in the transport of proteins and permit cells to survive under stresses such as heat shock and glucose starvation. Among the molecular chaperones (Gething et al., *Nature* 1992; 355:33-45; Caplan, *Trends Cell. Biol.* 1999; 9:262-268; Lin et al., *Mol. Biol. Cell.* 1993; 4:109-1119; Bergeron et al., *Trends Biochem. Sci.* 1994; 19:124-128), Bip (immunoglobulin heavy-chain binding protein, Grp78) is the best characterized chaperone of the ER (Haas, *Curr. Top. Microbiol. Immunol.* 1991; 167:71-82). Like other molecular chaperones, Bip interacts with many secretory and membrane proteins within the ER throughout their maturation, although the interaction is normally weak and short-lived when the folding proceeds smoothly. Once the native protein conformation is achieved, the molecular chaperone no longer interacts with the protein. Bip binding to a protein that fails to fold, assemble or be properly glycosylated, becomes stable, and is usually followed by degradation of the protein through the ER-associated degradation. This process serves as a "quality control" system in the ER, ensuring that only those properly folded and assembled proteins are transported out of the ER for further maturation, and improperly folded proteins are retained for subsequent degradation (Hurtley et al., *Annu. Rev. Cell. Biol.* 1989; 5:277-307).

Certain missense mutations result in amino acid substitutions that alter the native and proper folding of the protein. To correct these misfoldings, investigations have attempted to use various molecules as artificial chaperones. High concentrations of glycerol, dimethylsulfoxide, trimethylamine N-oxide, or deuterated water have been shown to stabilize the mutant protein and increase the intracellular trafficking of mutant protein in several diseases (Brown et al., *Cell Stress Chaperones* 1996; 1:117-125; Burrows et al., *Proc. Natl. Acad. Sci. USA.* 2000; 97:1796-801). These compounds are considered non-specific chemical chaperones to improve the general protein folding, although the mechanism of the function is still unknown. The high dosage of this class of compounds required for efficacy makes them difficult or inappropriate to use clinically, although they are useful for the biochemical examination of folding defect of a protein intracellularly. They also lack specificity.

Active Site Specific Chaperones for Enzymes

Co-owned U.S. Pat. Nos. 6,274,597, and 6,774,135 which are incorporated herein by reference, disclose a novel therapeutic strategy for Fabry disease, a lysosomal storage disorder (LSD) caused by a deficiency in lysosomal α-galactosidase A (α-Gal A) activity. α-Gal A deficiency often results from mutations in the gene that encode mutant proteins that result in folding defects. It was discovered that administration of 1-deoxygalactonojirimycin (DGJ), a potent competitive inhibitor of α-Gal A, effectively increased in vitro stability of a mutant α-Gal A (R301Q) at neutral pH. These results were also observed in lymphoblasts established from Fabry patients with the R301Q or Q279E mutations. Surprising, cultivation of the cells with DGJ at sub-inhibitory concentrations resulted in a substantial increase of residual enzyme activity. Furthermore, oral administration of DGJ to transgenic mice overexpressing a mutant (R301Q) α-Gal A substantially elevated the enzyme activity in major organs (Fan et al., *Nat. Med.* 1999; 5:112-115).

The principle of this strategy is as the follows. Since the mutant enzyme appears to fold improperly in the ER where pH is neutral, as evidenced by its instability at pH 7.0 in vitro (Ishii et al., *Biochem. Biophys. Res. Comm.* 1993; 197:1585-1589), the enzyme would be retarded in the normal transport pathway from the ER to the Golgi apparatus and subjected to rapid degradation. If a mutant enzyme could be efficiently transported to the lysosomes, it may retain normal or near normal kinetic properties and would remain active, because the mutant enzyme is sufficiently stable below pH 5.0. The goal, therefore, was to induce the mutant enzyme to adjust the proper conformation in the ER. In particular, a compound that can induce a stable molecular conformation of the enzyme could serve as an "active-site specific chaperone" (ASSC) or "pharmacological chaperone" to stabilize the mutant enzyme in a proper conformation for transport to the lysosomes. In the case of enzymes, such a compound unexpectedly was discovered to be a competitive inhibitor of the enzyme. Competitive inhibitors of an enzyme are known to occupy the catalytic site of the properly folded enzyme, resulting in stabilization of its correct conformation in vitro. It was found that they also serve as ASSCs or pharmacological chaperones to induce the proper folding of enzyme in vivo, thus rescuing the mutant enzyme from the ER quality control system.

Co-owned U.S. Pat. Nos. 6,583,158, 6,589,964, 6,599,919, and U.S. application Ser. No. 10/304,395 to Fan et al., exemplify the ASSC strategy with numerous other lysosomal storage diseases, including Gaucher disease. These findings demonstrate that this therapeutic strategy of using potent competitive inhibitors as ASSCs to increase the residual enzyme activity in the patient's cells is not limited to Fabry disease, and can be applied to enzyme deficiency diseases of this sort, and particularly to lysosomal storage disorders. In general, effective ASSCs of specific enzymes associated with particular diseases are potent competitive inhibitors of the enzyme. Unexpectedly, a more potent inhibitor of the enzyme acts as a better ASSC for the mutant enzyme (Fan, *Trends Pharmacol Sci.* 2003; 24:355-60).

Potent Inhibitors of β-glucocerebrosidase

β-Glucocerebrosidase (GCase, or acid β-glucosidase) is a lysosomal hydrolase that catalyzes the hydrolytic cleavage of glucose from glucosylceramide (Brady et al., *Biochem. Biophys. Res. Commun.* 1965; 18:221-225). The deficiency of the enzyme activity results in progressive accumulation of glucosylceramide, a normal intermediate in the catabolism of globoside and gangliosides, in lysosomes of macrophages, leading to Gaucher disease, the most common lysosomal storage disorder (Beutler et al., in The Metabolic and Molecular Bases of Inherited Disease, 8th ed., McGraw-Hill, New York 2001, 3635-3668).

Details regarding the disease and therapeutic treatment will be described herein below. Sawkar et al. have reported that the addition of an inhibitor of GCase to a fibroblast culture medium leads to a 2-fold increase in the activity of N370S GCase, indicating that a potent inhibitor of GCase may be of therapeutic interest in the treatment of Gaucher disease, although the particular inhibitor was not sufficient enough as a therapeutic agent because of high cytotoxocity (Sawkar A. R. et al., *Proc Natl Acad Sci USA.* 2002; 99(24): 15428-33). Therefore, effort has been taken to design and synthesize potent inhibitors for GCase.

The catalytic mechanism of β-glycosidases is believed to proceed via a covalent glycosyl-enzyme intermediate and positive charge generated at the anomeric position (Ichikawa et al., *J. Am. Chem. Soc.* 1998; 120:3007-3018; Heightman et al., 1999; *Angew. Chem. Int. Ed.* 1999; 38:750-770). Ichikawa et al. have designed a class of potent inhibitors for β-glycosidases, 1-N-iminosugars in which a nitrogen atom is at the anomeric position of a monosaccharide (Structure 1A, Isofagomine or hydroxy-piperidine). In a preliminary study, D-glucose-type 1-N-iminosugar (isofagomine, or hydroxypiperidine 1) has been shown to be a potent inhibitor of GCase (U.S. Pat. No. 6,583,158 to Fan et al.). N-alkyl derivatives of 1-deoxynojirimycin (DNJ) are also potent inhibitors of GCase, particularly those have longer alkyl group (greater than $C_6$ alkyl chain), although DNJ itself and those N-alkyl DNJ with shorter chains are not inhibitory (Structure 1B, N-nonyl 1-deoxynojirimycin) (U.S. Pat. No. 6,583,158). However, these inhibitors are either not specific enough or not potent enough towards to the GCase and not suitable for the treatment of Gaucher disease. Based on these findings, it was realized that GCase may contain two substrate binding sites in the catalytic domain: one which recognizes the glucosyl residue; the other which recognizes the ceramide moiety (Structure 1C, 6-C-nonyl hydroxypiperidine, RD-1: recognition domain 1; RD-2: recognition domain 2.). Determination of the crystal structure of GCase revealed an annulus of hydrophobic residues surrounding the entrance to the monosaccharide binding site (Dvir et al., *EMBO reports* 2003; 4:1-6), suggesting that a hydrophobic moiety attached to a sugar residue with a long alkyl chain is required for the interaction to the hydrophobic amino acid residues.

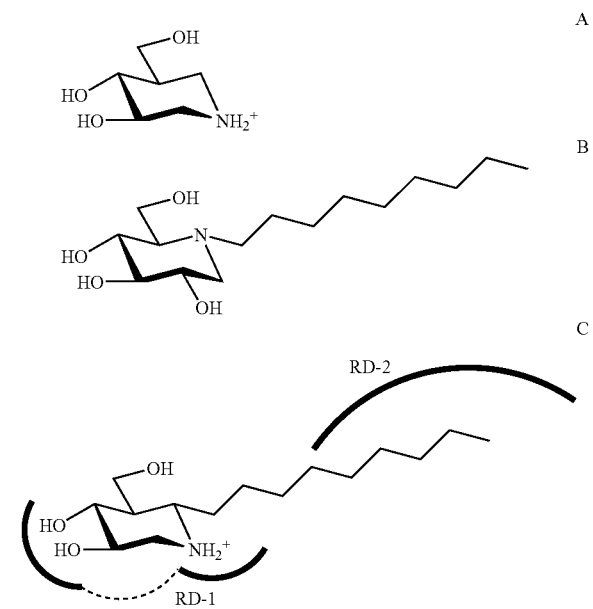

Structure 1. Potent inhibitors of human GCase.

1(A) Isofagomine or hydroxy-piperidine; 1(B) N-nonyl 1-deoxynojirimycin; 1(C) 6-C-nonyl hydroxypiperidine, RD-1: recognition domain 1; RD-2: recognition domain 2.

Thus, there remains a need in the art to design or identify specific competitive inhibitors of enzymes, and evaluate them for their ability to act as chaperones for the corresponding mutant enzymes that are associated with numerous LSDs, particularly inhibitors of GCase associated with Gaucher disease, and other disorders resulting from misfolded proteins.

SUMMARY OF THE INVENTION

The present invention provides a compound of the Formula I:

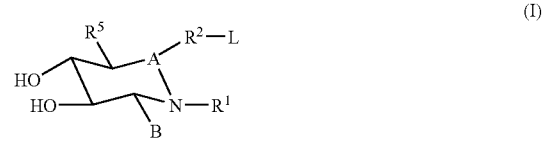

wherein A, B, $R^1$, $R^2$, $R^5$ and L are described herein below. The present invention also provides salts, esters and prodrugs of the compounds of Formula I.

Additionally, the present invention described methods of synthesizing compounds according to Formula I.

The present invention further provides a method of enhancing in a mammalian cell the activity of GCase, by contacting the cell with a compound of Formula I in an amount effective to enhance the activity of GCase, i.e., a non-inhibitory amount.

The present invention also provide a method of stabilizing in mammalian cell the GCase, by contacting the cell with a compound of Formula I in an amount effective to stabilize the GCase.

The present invention also provides compositions comprising a compound of Formula I and a pharmaceutically acceptable carrier.

Also provided is a method for treating Gaucher disease by administering to an individual in need of such treatment a pharmaceutical composition comprising a compound of Formula I in an amount effective to enhance the activity of GCase.

In addition, the present invention provides a method of inhibiting GCase in a mammalian cell when used at an inhibitory concentrations, by contacting the cell with a compound of Formula I.

The present invention provides a method of inhibiting GCase in vitro when used at an inhibitory concentrations, by contacting the enzyme with a compound of Formula I.

The present invention provides a method of inhibiting β-glucosidases in a mammalian cell when used at an inhibitory concentrations, by contacting the cell with an inhibitory concentration of a compound of Formula I.

The present invention provides a method of inhibiting β-glucosidase in vitro when used at an inhibitory concentrations, by contacting the enzyme with a compound of Formula I.

DETAILED DESCRIPTION

Figure 1:
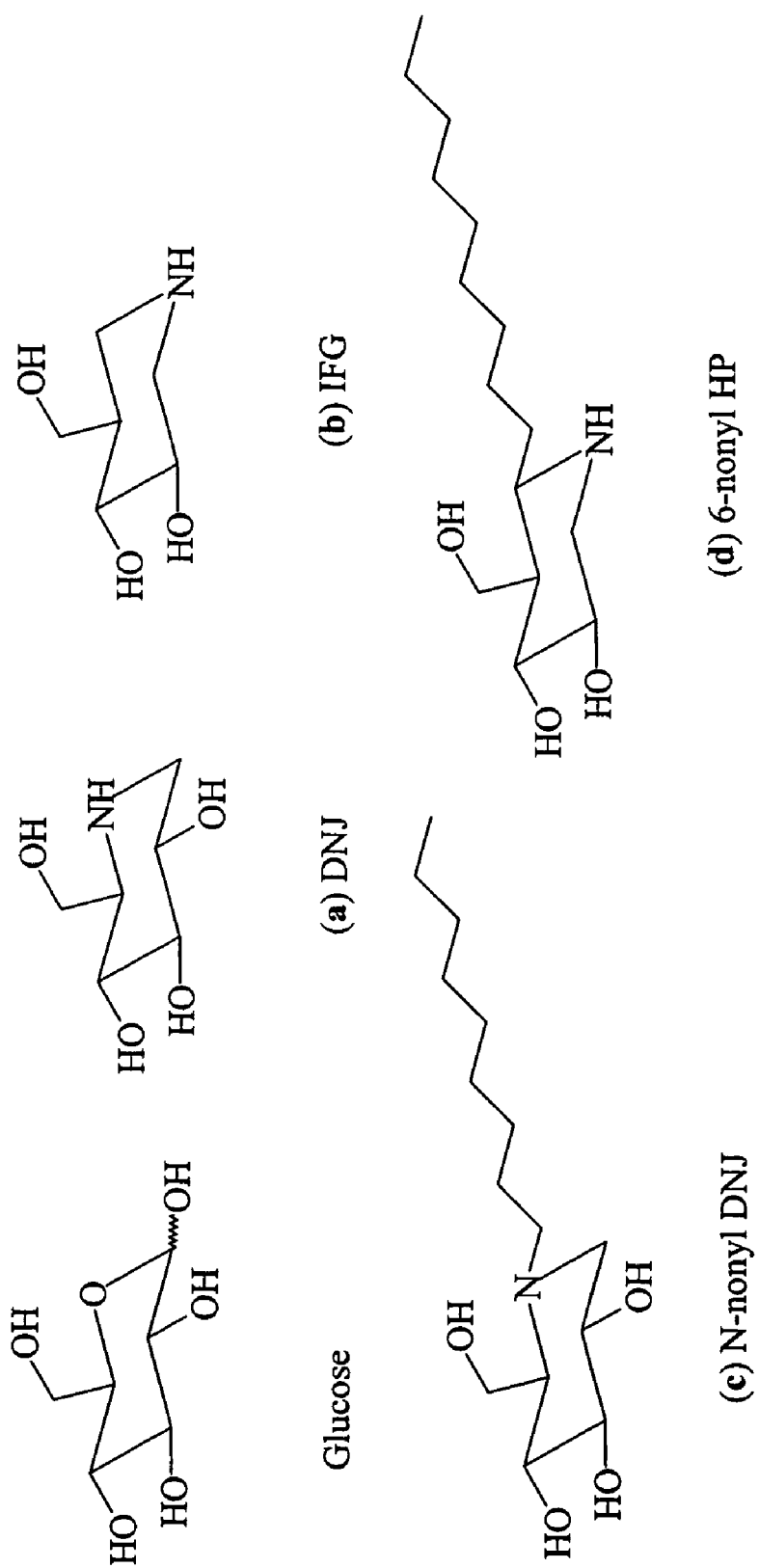
FIG. 1. Structures of GCase-specific compounds. (a) DNJ, 1-deoxynojirimycin; (b) IFG, isofagomine; (c) N-nonyl DNJ, N-nonyl 1-deoxynojirimycin; (d) 6-nonyl HP, or 6-nonyl isofagomine.

The present invention provides the design and synthesis of a novel class of potent competitive inhibitors of GCase, 6-alkyl hydroxy piperidine (HP) derivatives of glucose, and demonstrates their ability to increase the residual enzyme activity in fibroblasts from Gaucher patients with N370S mutation.

Gaucher Disease

Gaucher disease is a lysosomal storage disorder resulting from the deficient activity of β-glucocerebrosidase (hereinafter referred to as GCase) and the accumulation of its undegraded substrate, glucosylceramide (glucocerebroside), a normal intermediate in the catabolism of globoside and gangliosides (Beutler et al., *The Metabolic and Molecular Bases of Inherited Disease,* 8th ed. 2001; Scriver, C. R., Beaudet, A. L., Sly, W. S. and Valle, D., ed.) pp. 3635-3668, McGraw-Hill, New York). In some cases, the deficient activity of GCase is caused by mutations in the GCase gene, resulting in misfolding and subsequent degradation of the gene product in the ER. On the basis of the extent, and age of onset of primary neurological involvement, three clinical phenotypes are generally distinguished: (i) the non-neuronopathic variant (type 1, or adult form); (ii) the acute neuronopathic variant (type 2, or infantile form); and (iii) the subacute neuronopathic variant (type 3 or juvenile form). Type 1 Gaucher disease characterized by hepatosplenomegaly, secondary hypersplenism, and skeletal involvement is the most prevalent form and the severity and clinical course of this variant is particularly heterogeneous, ranging from early onset to no clinical manifestations (Grabowski, *Gaucher disease: Enzymology, genetics, and treatment.* 1993, Plenum Press, New York). In contrast, patients with the neurologic forms (types 2 and 3) are rare. The correlation of clinical severity and genotypes indicates that mild mutations presenting residual enzyme activity often result in type 1 disease, whereas severe or null mutations cause type 3 or type 2 disease.

Gaucher patients have been found from all regions of the world. Particularly, the disease is most common in the Ashkenazi Jewish population, where the frequency of Gaucher disease-causing alleles is approximately 0.0343 (Beutler et al., supra). The incidence is estimated as 1:4,000 (Mathoth et al., *Am J Med Genet.* 1987; 27: 561-5). Approximately 97% of GCase mutations in Ashkenazi Jews and 75% of the GCase mutations in non-Jewish populations can be detected by screening for the five most common mutations. Of many mutations that have now been documented, the N370S mutation which results in exclusively type 1 Gaucher disease is the most common mutation and is reported to be present in about 6% of the Ashkenazi Jewish population (Beutler et al., *Blood* 1992; 79: 1662-6). The L444P mutation which causes type 3 disease among homozygotes, exists at polymorphic levels in northern Sweden (Dahl et al., *Am J Hum Genet.* 1990; 47: 275-8). An insertion of a G at nucleotide position 84 of the cDNA is the second common Jewish mutation. It is found in approximately 0.6% of the Jewish population. This mutation results in a frameshift even before the N-terminus of the mature protein, and an allele bearing this mutation produces no enzyme activity and results in type 2 disease (Beutler et al., *Proc Natl Acad Sci USA.* 1991; 88: 10544-7).

The gene coding for GCase has been mapped to chromosome 1 at q21 (Ginns et al., *Proc Natl Acad Sci USA* 1985; 82:7101-5). The gene for GCase is approximately 7 kb in length and contains 11 exons. GCase cDNA is about 2 kb in length, and active enzyme can be produced from in vivo translation of the cDNA in a variety of eukaryotic cells, including COS cells and insect cells infected with baculovirus (Grabowski et al., *Enzyme* 1989; 41: 131-42). Human GCase is a homomeric glycoprotein. The mature polypeptide is 497 amino acids with a calculated molecular mass of 55,575. The glycosylated enzyme from placenta has a molecular weight of about 65 kD. Saposin C activates GCase in vitro in the presence of negatively charged phospholipids.

Current treatment. Enzyme replacement therapy is currently available to type 1 Gaucher patients. Intravenous infusion of human placental GCase or recombinant GCase (modified to expose covered mannose residues) has been shown to be effective at reversing many characteristic clinical manifestations in type 1 Gaucher patients (Kay et al., *Trans Assoc. Am. Phys.* 1991; 104: 258-264; and Grabowski et al., *Pediatr. Res.* 1993; 33: 139A). For the type 2 or type 3 patients having neurological involvement, the enzyme replacement therapy (ERT) is less effective, since the enzymes do not cross the blood brain barrier after intravenous infusion.

Another approach to the treatment of Gaucher disease is the use of inhibitors of GCase to lower the levels of glucosylceramide and glycolipids (Inokuchi et al., *Lipid Res.* 1987; 28: 565-71; Platt et al., *Biochem. Pharmacol.* 1998; 56: 421-430; and Radin et al., *Glycoconjugate J.* 1996; 13: 153-157). This is known as substrate reduction therapy (SRT). A modest improvement of clinical symptoms in patients was observed after one-year treatment (Cox et al., *Lancet* 2000; 355: 1481-1485) with small molecule glucose derivatives. SRT, which uses small molecule inhibitors to prevent the synthesis of pathogenic substrates, is under evaluation for several LSDs, and N-butyl 1-deoxynojirimycin (NB-DNJ) has conditional marketing approval in Europe and the U.S. for the treatment of Gaucher disease (Butters et al., *Philos Trans R Soc Lond B Biol Sci.* 2003; 358:927-945.). One advantage of this as compared to ERT is that the small molecule inhibitors may potentially cross the blood brain barrier and prevent substrate accumulation in the brain. The most frequent adverse effect was diarrhea, which occurred in 79% of patients shortly after the start of the treatment. It is uncertain whether the long-term reduction of glycolipids will have other adverse effects.

As discussed above, another small molecule approach recently developed is known as active site specific chaperone (ASSC) therapy (Fan et al., *Nat Med.* 1999; 5: 112-115; Fan, *Trends Pharmacol Sci.* 2003; 24: 355-360). ASSC uses low concentrations of potent enzyme inhibitors, which are specific for the mutant (or wild type) enzyme, to enhance the folding and activity of the mutant proteins in patients with LSDs. Since the active site inhibitors used in ASSC are specific for the disease-causing enzyme, the therapy is targeted to a single protein and a particular metabolic pathway, unlike SRT which inhibits an entire synthetic pathway. Like SRT, the small molecule inhibitors for ASSC have the potential of crossing the blood brain barrier and therefore could be used to treat neurological LSD forms.

Design and Synthesis of Potent Inhibitors for GCase and Effective ASSCs for Gaucher Disease.

A more potent inhibitor of an enzyme acts as a better ASSC for the mutant enzyme (Fan, *Trends Pharmacol Sci.* 2003; 24:355-60). Accordingly, the present invention designed and synthesized a novel class of potent inhibitors for GCase, and used these inhibitors as ASSCs for the enhancement of residual enzyme activity in cells derived from Gaucher patients.

Fan et al. have also determined that ASSC therapy can be used to treat Gaucher disease using glucoimidazole (GIZ) and polyhydroxycyclohexenyl amine (PHCA) derivatives, which may be administered to individuals having Gaucher disease as "active-site specific chaperones" for the mutant glucocerebrosidase associated with the disease. (U.S. Patent Application entitled Glucoimidazole and Polyhydroxycyclohexenyl Amine Derivatives to Treat Gaucher Disease, filed Nov. 12 2004.)

In addition to enhancing the activity of the mutant (or wild type) enzymes associated with the LSDs, the ASSCs have also been demonstrated to enhance the activity of the corresponding wild-type enzyme (see U.S. Pat. No. 6,589,964 to Fan et al.), thus suggesting their use in co-therapy for enzyme replacement therapy and in gene therapy in LSD patients.

The present invention also contemplates the inhibition of β-glucocerebrosidase (GCase). Such inhibition is useful, for example, for studying the effects of a lack of b-glucocerebrosidase in animal models. Since targeted deletion of β-glucocerebrosidase in mammals is lethal, since the knockout mice cannot be generated for the purposes of evaluating the Gaucher disease state. The present invention contemplates administering an inhibitory amount of the β-glucosidase inhibitors to animals to mimic the Gaucher disease phenotype.

DEFINITIONS

As used herein, the following terms have the following definitions.

Chemical

The term 'alkyl' refers to a straight or branched $C_1$-$C_{20}$ hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl). The alkyls used herein are preferably $C_1$-$C_8$ alkyls.

The term "alkenyl" refers to a $C_2$-$C_{20}$ aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "alkynyl" refers to a $C_2$-$C_{20}$ straight or branched chain hydrocarbon radicals having at least one carbon-carbon triple bond, e.g. ethynyl, propynyl, butnyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronapththyl, adamantyl and norbornyl groups bridged cyclic group or spriobicyclic groups, e.g., spiro (4,4) non-2-yl.

The term "cycloalkenyl" refers to cyclic ring-containing radicals containing 3 to about 14 carbon atoms, system such as cyclopropenyl, cyclobutenyl, cyclopentenyl, cyclohexenyl.

The term "cycloalkalkyl" refers to a cycloalkyl as defined above directly attached to an alkyl group as defined above, that results in the creation of a stable structure such as cyclopropylmethyl, cyclobutylethyl, cyclopentylethyl.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —CH$_2$C$_6$H$_5$, and —C$_2$H$_4$C$_6$H$_5$.

The term "heterocyclic ring" and "heterocyclyl" refer to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The heterocyclic ring radical may be attached to the main structure at any heteroatom or carbon atom that results in the creation of a stable structure.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The substituents in the 'substituted alkyl', 'substituted alkenyl' 'substituted alkynyl' 'substituted cycloalkyl' 'substituted cycloalkalkyl' 'substituted cyclocalkenyl' 'substituted arylalkyl' 'substituted aryl' 'substituted heterocyclic ring', 'substituted heteroaryl ring,' 'substituted heteroarylalkyl', or 'substituted heterocyclylalkyl ring', may be the same or different with one or more selected from the groups hydrogen, hydroxy, halogen, carboxyl, cyano, amino, nitro, oxo (═O), thio (═S), or optionally substituted groups selected from alkyl, alkoxy, alkenyl, alkynyl, aryl, arylalkyl, cycloalkyl, aryl, heteroaryl, heteroarylalkyl, heterocyclic ring, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(═N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O) OR$^y$—, —OC(O)R$^x$, —OC(O)NR$^x$R$^y$, —R$^x$NR$^y$R$^z$, —R$^x$R$^y$R$^z$, —R$^x$CF$_3$, —R$^x$NR$^y$C(O)R$^z$, —R$^x$OR$^y$, —R$^x$C(O) OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, —ONO$_2$, wherein R$^x$, R$^y$ and R$^z$ in each of the above groups can be hydrogen atom, substituted or unsubstituted alkyl, haloalkyl, substituted or unsubstituted arylalkyl, substituted or unsubstituted aryl, substituted or unsubstituted cycloalkyl, substituted or unsubstituted cycloalkalkyl substituted or unsubstituted heterocyclic ring, substituted or unsubstituted heterocyclylalkyl, substituted or unsubstituted heteroaryl or substituted or unsubstituted heteroarylalkyl.

The term "lipophilic" refers to a functional residue capable of interacting with hydrophobic amino acid residues. Examples of liphophilic groups include but are not limited to C$_1$-C$_2$ substituted or unsubstituted alkyl, substituted or unsubstituted alkenyl, substituted or unsubstituted alkynyl, substituted or unsubstituted cycloalkyl; substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; and substituted or unsubstituted heteroarylalkyl.

The term "halogen" refers to radicals of fluorine, chlorine, bromine and iodine.

The term "hydrogenatable protecting group" refers to protecting groups capable of removal by hydrogenating conditions, for example, benzyl and 4-methoxybenzyl.

The term "acid" refers to Lewis acid such as sulfuric acid, hydrochloride or hydrochloride generated by reaction of acid chloride with alcohol.

The term "organic acid" refers to organic Lewis acid such as p-toluenesulfonic acid, camphorsulfonic acid.

The term "crown ether" refers to large ring compounds containing several oxygen atoms in a regular pattern such as 12-crown-4, 15-crown-5, 18-crown-6, dicyclohexano-18-crown-6.

The term "organometallic reagent" refers to a compound that contains a bond between a carbon and a metal atom, such as organolithium, organozinc, organocopper, Grignard reagents.

The term "hydrogenolysis conditions" refers to catalytic hydrogenolysis using catalyst such as, but not limited to, Pd(OH)$_2$/C, Pd/C, Pt or Raney nickel in the presence of a hydrogen source.

The term "hydrogenation" refers to a chemical reaction in which unsaturated bond between carbon atoms are reduced by attaching a hydrogen atom to each other using catalyst such as, but not limited to, Pd(OH)$_2$/C, Pd/C, Pt or Raney nickel in the presence of a hydrogen source.

The term "reducing agent" refers to an agent converting a functional group in a molecule from one oxidation state to lower one, such as LiAlH$_4$, NaBH$_4$, Zn(BH$_4$)$_2$, i-Bu$_2$AlH and Li-s-Bu$_3$H.

The term "leaving group" refers to a group that can be substituted by nucleophilic reagent, such as TsO—, TfO—, MsO—, Cl, Br, I.

The term "N-protecting group" refers to groups temporarily protecting amine or imine group to avoid further sites of reaction, such as, but not limited to, 4-methoxybenzyl, benzyl, tert-butyloxycarbonyl, benzyloxycarbonyl.

The term "O-protecting group" refers to groups temporarily protecting an hydroxy to avoid further sites of reaction, such as, but not limited to, 4-methoxybenzyl, benzyl, and trimethylsilyl.

The term "base" refers to organic Lewis base, such as pyridine, triethylamine, diisopropylethylamine.

The term "nucleophilic moiety and nucleophilic reagent" refer to a reagent that forms a bond to its reaction partner (the electrophile) by donating both bonding electrons, such as metal salt of an alcohol, thiol, or 1-alkyne.

The term "a short flexible linker" refers to linkers with linear length of about 6 Å to about 12 Å, preferably about 9 Å.

Biological

As used herein, the term "active site specific chaperone" (ASSC) refers to any molecule including but not limited to a protein, peptide, nucleic acid, carbohydrate, that specifically interacts reversibly with an active site of a protein and enhances formation of a stable molecular conformation. As used herein, "ASSC" does not include endogenous general chaperones present in the ER of cells such as Bip, calnexin or calreticulin, or general, non-specific chemical chaperones such as deuterated water, DMSO, or TMAO.

As used herein, the term "active site" refers to the region of a protein that binds a substrate or binding partner and contributes the amino acid residues that directly participate in the making and breaking of chemical bonds. According to the present invention, the active site encompasses the catalytic domain of the GCase.

The term "wild-type activity" refers to the normal physiological function of a GCase. in a cell. Such functionality can be tested by any means known to establish functionality of a protein, specifically, an enzyme. Certain tests may evaluate attributes of a protein that may or may not correspond to its actual in vivo function, but nevertheless are aggregate surrogates of protein functionality, and wild-type behavior in such tests is an acceptable consequence of the protein folding rescue techniques of the invention. One such activity in accordance with the invention is appropriate transport from the endoplasmic reticulum to the particular destination of GCase in the cell, i.e., the lysosome.

The term "functional GCase protein" refers to a GCase protein that has the ability to fold in a proper conformation, achieve its native location in the cell, and have catabolic activity towards glucocerebroside and other lipid substrates. A functional GCase protein includes wild-type GCase proteins (see definitions below), e.g., as depicted in SEQ ID NO: 2.

As used herein, the term "mutant GCase" refers to a GCase translated from a gene containing one or more genetic mutations that result in an altered protein sequence that does not achieve its native conformations under the conditions normally present in the ER. The failure to achieve this conformation results in the GCase being degraded, rather than being transported through its normal pathway in the protein transport system to its proper location within the cell.

Some specific embodiments of such GCase mutations are the N370S mutation and the L444P mutation.

The term "enhancing the activity" of GCase means stabilizing a proper conformation of a mutant GCase protein in the ER so that it folds in a proper conformation, achieves its native location in the cell, and has catabolic activity towards cerebroside, its lipid substrate). This term also refers to increasing the wild-type activity of an exogenously administered GCase protein, i.e., by increasing the stability and extending the in vivo half-life of wild-type GCase, thus, prolonging its activity.

The term "stabilize a proper conformation" refers to the ability of a compound of the invention to induce or stabilize the conformation of a mutated GCase, regardless whether in the ER or other cellular compartments, that is functionally identical to the conformation of the wild type enzyme. By "functionally identical", the invention means that there may be minor variations in the conformation (indeed almost all proteins exhibit some conformational flexibility in their physiological state) but that conformational flexibility does not result in (1) aggregation, (2) elimination through the endoplasmic reticulum-associated degregation, (3) impairment of enzyme function, and/or (4) improper transport within the cell. This term also refers to the ability of a compound to stabilize a proper conformation of wild-type GCase in viov following exogenously added GCase, or an vitro in a formulation of enzyme.

A "wild-type GCase gene" refers to nucleic acid sequences which encode an ASM protein capable of having functional biological activity in vivo. The wild-type GCase nucleic acid sequence may contain nucleotide changes that differ from the known, published sequence, e.g., SEQ ID NO: 1, as long as the changes result in amino acid substitutions that have little or no effect on the biological activity. As used herein, the term wild-type may also include GCase nucleic acid sequences engineered to encoding a GCase protein capable of increased or enhanced activity relative to the endogenous or native GCase protein.

A "wild-type GCase protein" refers to any protein encoded by a wild-type gene that is capable of having functional biological activity when expressed or introduced in vivo.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization*; B. D. Hames & S. J. Higgins eds. (1985); *Transcription And Translation* (B. D. Hames & S. J. Higgins, eds. 1984); *Animal Cell Culture* (R. I. Freshney, ed. 1986); *Immobilized Cells And Enzymes*; IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994).

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein, may be associated with other proteins or nucleic acids, or both, with which it associates in the cell, or with cellular membranes if it is a membrane-associated protein. In a specific embodiment, an isolated GCase protein is a recombinant GCase protein expressed from an expression vector. An isolated material may be, but need not be, purified.

The term "purified" as used herein refers to material that has been isolated under conditions that reduce or eliminate unrelated materials, i.e., contaminants. For example, a purified GCase protein is preferably substantially free of other proteins or nucleic acids with which GCase is normally associated in a cell. As used herein, the term "substantially free" is used operationally, in the context of analytical testing of the material. Preferably, purified ASM substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

The term "host cell" means any cell of any organism that is selected, modified, transformed, grown, or used or manipulated in any way, for the production of a substance by the cell, for example the expression by the cell of a mutant or functional mammalian GCase gene, including a DNA or RNA sequence, or the GCase enzyme. Host cells can further be used for preliminary evaluation of the ASSC concept other assays. A "recombinant DNA molecule" is a DNA molecule that has undergone a molecular biological manipulation or engineering.

A "gene" is a sequence of nucleotides which code for a "gene product". Generally, a gene product is a protein. However, a gene product can also be another type of molecule in a cell, such as an RNA (e.g., a tRNA or a rRNA). For the purposes of the present invention, a gene product also refers to an mRNA sequence which may be found in a cell. As used herein, a gene refers to the nucleotide sequences encoding wild-type or mutant GCase.

The term "express" and "expression" means allowing or causing the information in a GCase gene or DNA sequence to become manifest, for example producing RNA (such as rRNA or MRNA) or a GCase protein by activating the cellular functions involved in transcription and translation of a corresponding GCase gene or DNA sequence, i.e., sequences encoding GCase. A GCase DNA sequence is expressed by a cell to form an "expression product" such as a GCase RNA (e.g., an mRNA or an rRNA) or a GCase protein. The expression product itself, e.g., the resulting GCase RNA or protein, may also be said to be "expressed" by the cell.

The term "transfection" means the introduction of a foreign nucleic acid into a cell. The term "transformation" also means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species. As used herein, transfection or transformation will include introduction of sequences encoding functional GCase in individuals having mutated endogenous GCase genes.

The terms "vector", "cloning vector", and "expression vector" mean the vehicle by which a GCase DNA or RNA sequence (e.g., a foreign gene) can be introduced into a host cell so as to transform the host and promote expression (e.g., transcription and translation) of the introduced sequence. Vectors include any genetic element, such as a plasmid, phage, transposon, cosmid, chromosome, virus, virion, etc., which is capable of replication when associated with the proper control elements and which can transfer GCase gene sequences between cells. Thus, the term includes cloning and expression vehicles, as well as viral vectors.

The term "expression system" means a host cell and compatible vector under suitable conditions, e.g. for the expression of a GCase protein coded for by foreign DNA carried by the vector and introduced to the host cell. Common expression systems include E. coli host cells and plasmid vectors, insect host cells such as Sf9, Hi5 or S2 cells and Baculovirus vectors and expression systems, and mammalian host cells and vectors.

The term "gene therapy" refers to a method of changing the expression of an endogenous gene by exogenous administration of a gene, i.e., a GCase gene. As used herein, gene therapy also refers to the replacement of a defective GCase gene, or replacement of a missing GCase gene, by introducing a functional gene corresponding to the defective or missing GCase gene into somatic or stem cells of an individual in need. Gene therapy can be accomplished by "ex vivo" methods, in which differentiated or somatic stem cells are removed from the individual's body followed by the introduction of a normal copy of the defective gene into the explanted cells using a viral vector as the gene delivery vehicle. In addition, in vivo direct gene transfer is gene transfer into cells in the individual in situ using a broad range of viral vectors, liposomes, protein DNA complexes, or naked DNA in order to achieve a therapeutic outcome.

The term "recombinant protein" refers to a GCase protein (gene product) encoded by a therapeutic GCase gene carried on a vector. Generally, the cell receiving the vector will lack expression and/or activity of any endogenous GCase protein corresponding to the recombinant protein, or if there is expression of such an endogenous GCase protein, it is of a mutant or at a very low level. In one embodiment, the recombinant protein is produced by a cell in tissue culture for experimental and therapeutic purposes. In another embodiment, the recombinant protein is produced in vivo from cells transformed with vector, wherein the vector or the cells comprising the vector have been administered to a subject, i.e., gene therapy. The recombinant GCase protein will likely be indistinguishable from wild-type protein in normal individuals, i.e., individuals who are not deficient in the protein or do not have Gaucher disease.

Therapeutic and Administration

A "subject" or "patient" is a human or an animal that has developed, or is likely to develop Gaucher disease, more particularly a mammal, preferably a rodent or a primate, and most preferably a human. In one embodiment, the patient is a member of the Ashkenazi Jewish population who has been diagnosed with, or who has been identified as having an increased risk of developing Gaucher disease due inherited mutations in the GCase gene. However, the term "subject" encompasses anyone in the world having, or genetically at risk of developing, Gaucher disease.

The term "prevention" refers to the prevention of the onset of the disease, which means to prophylactically interfere with a pathological mechanism that results in the disease, e.g., Gaucher disease. In the context of the present invention, such a pathological mechanism can be an increase in mutant protein folding and expression of GCase.

The term "treatment" means to therapeutically intervene in the development of a disease in a subject showing a symptom of this disease. In the context of the present invention, these symptoms can include but are not limited to accumulation of GCase in lysosomes, hepatosplenomegaly, psychomotor retardation, pulmonary abnormalities degeneration of bones and joints, and progressive neurodegeneration.

The term "therapeutically effective amount" is used herein to mean an amount or dose of the HP derivative of the present invention that is sufficient to increase the level of mutant GCase expression, e.g., to about 3-5%, preferably by about 10%, and more preferably by about 30% of the level found in normal cells, i.e., cells from an individual not having Gaucher disease. Preferably, a therapeutically effective amount can ameliorate or prevent a clinically significant deficit GCase activity in the subject. Alternatively, a therapeutically effective amount is sufficient to cause an improvement in a clinically significant condition in the subject, e.g., amelioration of progressive neurodegeneration in Types 2 and 3 Gaucher patients.

The phrase "pharmaceutically acceptable" refers to molecular entities and compositions that are physiologically tolerable and do not typically produce an allergic or similar untoward reaction, such as gastric upset, and dizziness, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly, in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Novel Compounds and Synthesis

Compounds

According to the present invention, the ASSC is a 6-derivative (and optionally, additionally N-alkylated) of HP having (i) a positive charge at the position corresponding anomeric position of a pyranose ring; (ii) a short, flexible linker emanating from the corresponding position of the ring oxygen in a pyranose; and (iii) a lipophilic moiety connected to the linker. In a specific embodiment, the ASSC is 6-nonyl-HP, or (3R, 4R, 5R, 6S/6R)-5-(hydroxymethyl)-6-n-nonyl-3,4-dihydroxpiperdine. Because C-6 position of the glucose residue is not recognized by the most of GCase and β-glucosidases (De Bruyne et al. *Eur. J. Biochem.* 1979; 102:257-67), the substitutes at the C-6 position can be a hydrogen, hydroxy or hydroxymethyl.

More specifically, the present invention provides a novel compound of the following Formula I:

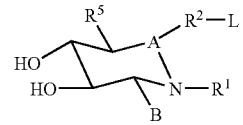

wherein A represents a carbon or nitrogen;

B is a hydrogen, hydroxyl, N-acetamide or a halogen;

$R^1$ is a hydrogen, substituted or unsubstituted: alkyl, alkenyl, alkynyl, cycloalkyl, cycloalkenyl, aryl, arylalkyl, heteroaryl, heterocyclic, heterocyclyalkyl, or heteroarylalkyl; —C(O)$R^3$ or —S(O)$_m R^3$. Preferably, $R^1$ comprises H or an organic moiety having 1-12 carbon atoms.

$R^2$ is an optional short, flexible linker with a linear length of from about 6 Å to about 12 Å. Alternatively, $R^2$ is a $C_1$-$C_6$ substituted or unsubstituted: alkyl, alkenyl, or alkynyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m$ $NR^3$.

$R^3$ is of hydrogen, or a substituted or unsubstituted: alkyl, alkenyl; alknyl; cycloalkyl, cycloalkenyl; aryl; arylalkyl; heteroaryl; heterocyclic; heterocyclyalkyl; or heteroarylalkyl. Preferably, $R^3$ comprises H or an organic moiety having 1-12 carbon atoms, or more preferably 1-6 carbon atoms.

m is 1 or 2, and $R^5$ is a hydrogen, hydroxyl, or hydroxymethyl.

L is a lipophilic group having 1-12 carbon atoms comprising a substituted or unsubstituted: alkyl, alkenyl, alkynyl; cycloalkyl, cycloalkenyl; aryl; arylalkyl; heteroaryl; heterocyclic; heterocycloalkyl; or heteroarylalkyl.

Also contemplated are pharmaceutically acceptable salts and prodrugs of the compound of Formula I.

Further preferred is when $R^1$ is hydrogen.

Further preferred is when $R^2$ is selected from the group consisting of $C_2$-$C_6$ substituted or unsubstituted alkyl optionally interrupted by one or more moieties chosen from the group consisting of NH, $NR^3$, and O; $C_2$-$C_6$ substituted or unsubstituted alkenyl optionally interrupted by one or more moieties chosen from the group consisting of NH, $NR^3$ and O; $C_2$-$C_6$ substituted or unsubstituted alkenyl optionally interrupted by one or more heteroatoms chosen from the group consisting of NH, NR³ and O; C₂-C₆ substituted or unsubstituted alkenyl optionally interrupted by one or more heteroatoms chosen from the group consisting of NH, NR³ and O.

Further preferred is when R² is chosen from the group consisting of

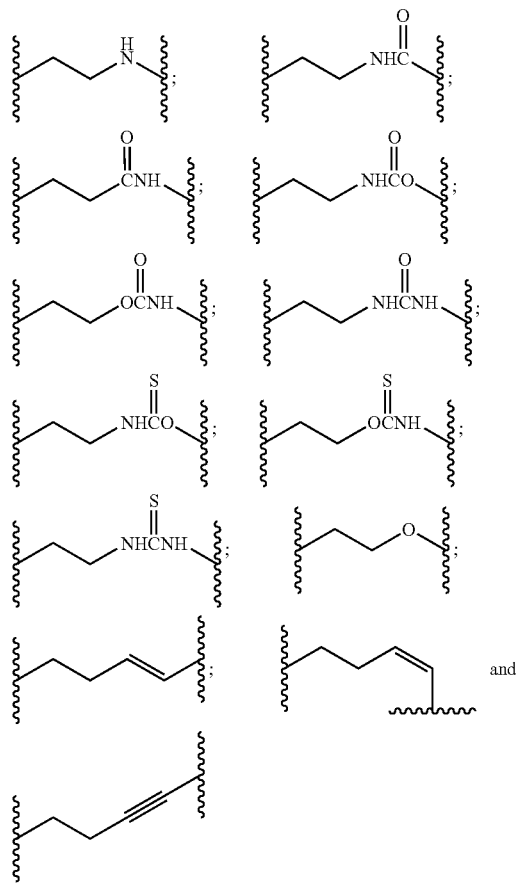

Further preferred is when R² is not present and L is unsubstituted C₁-C₂ alkyl.

Still further preferred is when R² is not present and L is unsubstituted C₆-C₁₂ alkyl.

Further preferred is when R² is not present and L is unsubstituted C₆ alkyl.

Further preferred is when R² is not present and L is unsubstituted C₇ alkyl.

Further preferred is when R² is not present and L is unsubstituted C₈ alkyl.

Further preferred is when R² is not present and L is unsubstituted C₉ alkyl.

Further preferred is when R² is not present and L is benzyl.

A further preferred compound of the invention is (3R,4R,5R,6S/6R)-5-(hydroxymethyl)-6-n-butyl-3,4-dihydroxypiperidine.

A further preferred compound of the invention is (3R,4R,5R,6S/6R)-5-(hydroxymethyl)-6-n-hexyl-3,4-dihydroxypiperidine.

A further preferred compound of the invention is (3R,4R,5R,6S/6R)-5-(hydroxymethyl)-6-n-heptyl-3,4-dihydroxypiperidine.

A further preferred compound of the invention is (3R,4R,5R,6S/6R)-5-(hydroxymethyl)-6-n-octyl-3,4-dihydroxypiperidine.

A further preferred compound of the invention is (3R,4R,5R,6S/6R)-5-(hydroxymethyl)-6-n-nonyl-3,4-dihydroxypiperidine.

A further preferred compound of the invention is (3R,4R,5R,6S/6R)-5-(hydroxymethyl)-6-benzyl-3,4-dihydroxypiperidine.

Collectively, the compounds of Formula I are referred to herein as "HP derivatives."

Compounds of the present invention include pharmaceutically acceptable salts and pro-drugs of Forumula I. Pharmaceutically acceptable salts forming part of this invention include salts derived from inorganic bases such as Li, Na, K, Ca, Mg, Fe, Cu, Zn, Mn; salts of organics such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. Pharmaceutically acceptable solvates may be hydrates or comprise other solvents of crystallization such as alcohols.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound with a suitable derivatizing agent. For example hydroxy groups can be converted into esters via treatment with a carboxilic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

Synthesis

Additionally, the present invention describes methods of synthesizing compounds according to Formula I comprising the steps of:
a) Reacting L-xylose with a hydrogenizable protecting group precursor compound in the presence of an acid to produce a compound of the Formula II:

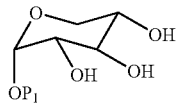

where $P^1$ is a hydrogenizable protecting group.
b) Reacting a compound according to Formula II with an acetal, hetal or cycloborate such as 2-methoxypropene or 1,1-dimethoxycyclohexane in the presence of an organic acid or inorganic catalyst to produce a compound of the Formula III:

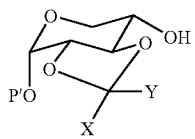

where X, Y=H, alkyl aryl cycloalkyl or may be linked via a C5-C6 alkyl group.
c) Reacting a compound according to Formula III with trifluoromethane sulfonic anydride in the presence of an organic base chosen from the group consisting of a tertiary amine or pyridine to produce a compound of the Formula IV:

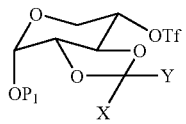

d) Reacting a compound according to Formula IV with MCN wherein M is chosen from the group consisting of Li, K and Na in the presence of a crown ether to produce a compound of the Formula V:

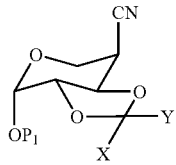

e) Reacting a compound according to Formula V with an organometalic reagent of the Formula VI:

L—$R^2M^2$ wherein $R^2$ and L are as described in claim 1 and $M^2$ is chosen from the group consisting of Mg Br; Mg Cl; Li; CuLi; ZnBr followed by reaction with a reducing agent to form a compound of the Formula VII:

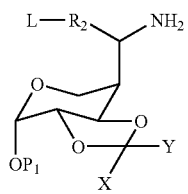

f) Deprotection and rearrangement the compound according to Formula VII followed by cyclization and reduction with hydrogenating conditions in the presence of a Lewis acid or inorganic catalyst to produce a compound of the Formula VIII (Formula VIII represents both of R and S configuration for L—$R^2$ substituted group):

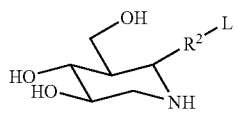

g) optionally reacting the compound according to Formula VIII with carbonyl compounds such as aldehyde or ketone in the presence of the reducing reagents such as sodium triacetoxyborohydride sodium cyanoborohydride, $H_2$/Pd/C or $H_2$/Pd(OH)$_2$/C or reacting with $R^1$X wherein $R^1$ is as described in claim 1 and X is a leaving group to produce a compound of the Formula IX:

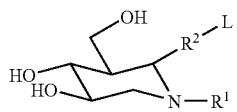

The present invention further describes an alternative method for the synthesis of compounds according to Formula I comprising the steps of:
a) Reacting L-xylose with a hydrogenizable protecting group precursor compound in the presence of an acid chloride to produce a compound of the Formula II:

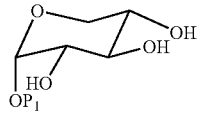

where $P^1$ is a hydrogenizable protecting group
b) Protecting a compound according to Formula II with acetals, ketals, or cyclicborates such as 2-methoxypropene, or 1,1-dimethoxycyclohexane in the presence of an organic or inorganic acid to produce a compound of the Formula III:

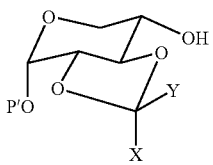

where X, Y=H, alkyl, aryl, cycloalkyl or may be linked via a $C_5$-$C_6$ alkyl group.

c) Reacting a compound according to Formula III with triflic anydride in the presence of a base chosen from the group consisting of a tertiary amine base and pyrdine to produce a compound of the Formula IV:

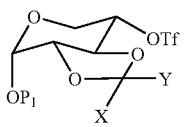

d) Reacting a compound according to Formula IV with MCN wherein M is chosen from the group consisting of Li, K and Na in the presence of a crown ether to produce a compound of the Formula V:

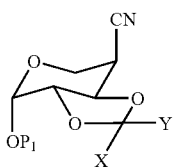

e) Reacting a compound according to Formula V with a compound of the Formula X:

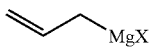

wherein X is chosen from the group consisting of Br and Cl; followed by reaction with a reducing agent to form a compound of the Formula XI:

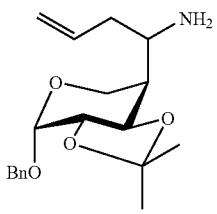

f) Protecting the amino group in the compound of Formula XI followed by ozonolysis of double bond, protection of aldehyde and hydrogenation to form a compound of the Formula XII:

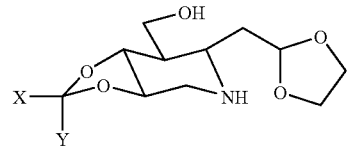

g) Selectively deprotecting the respective acetal, ketal or cycliborate group according to the Formula XII with aqueous acetic acid solution to produce a compound of the Formula XIII:

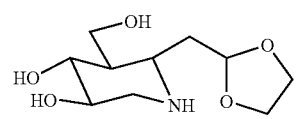

h) N and O-protecting with a protecting group such as 4-methoxybenzyl group to form a compound of the Formula XIV:

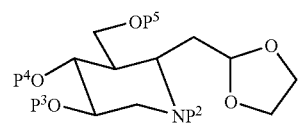

wherein $P^2$, $P^3$, $P^4$ and $P^5$ are the same or different protecting groups.

i) Hydrolysing a compound of Formula XIV under the acidic condition such as HOAc, HCl, $CF_3COOH$ to generate a compound of Formula XV:

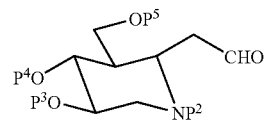

j) Reacting a compound of Formula XV with a reducing agent such as sodium borohydride, lithium aluminum hydride, followed by conversion of the resulting alcohol to a leaving group halo, OMs, OTf to form a compound of Formula XVI:

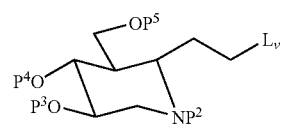

wherein Lv is a leaving group.

k) Reaction of a compound of Formula XV with amine under reducing condition or reaction of a compound of Formula XV with Wittig reagent or Reaction of a compound of Formula XVI with

wherein $R^6$ is a nucleophillic moiety chosen from the group consisting of

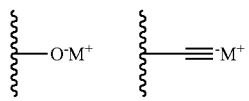

optionally followed by deprotection with ceric ammonium nitrate or $Pd(OH)_2/C/H_2$ to form a compound of Formula XVII (Formula XVII represents both of R and S configuration for linker lipophilic moiety):

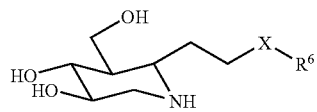

wherein X is chosen from the group consisting of O, NH, NHCOO, NHCONH, NHCSO, NHCSNH, CONH, NHCO, NR, S, $CH_2$, HC=CH; and C≡C.

The present invention further describes a method for the synthesis of compounds according to Formula XV:

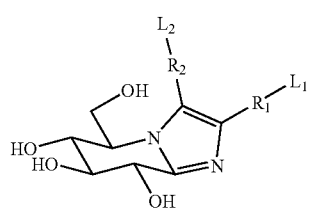

$R^1$ and $R^2$ optionally present are short, flexible linkers with a linear length of about 6 Å to about 12 Å, preferably about 9 Å. $R^1$ and $R^2$ can also be independently selected a $C_2$-$C_6$ substituted or unsubstituted: alkyl, alkenyl, or alkynyl optionally interrupted by one or more moieties chosen from the group consisting of NH, NHCOO, NHCONH, NHCSO, NHCSNH, CONH, NHCO, $NR^3$, O, S, $S(O)_m$ and $—S(O)_m NR^3$; and m is 1 or 2. In addition, $R^1$—$L^1$ or $R^2$—$L^2$ can be a hydrogen, if either $R^2$—$L^2$ or $R^1$—$L^1$ is other than a hydrogen.

$L^1$ and $L^2$ are lipophilic groups selected from the group consisting of $C_1$-$C_{12}$ substituted or unsubstituted alkyl, substituted or unsubstituted alkenyl, substituted or unsubstituted alkynyl; substituted or unsubstituted cycloalkyl; substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; substituted or unsubstituted heteroarylalkyl.

$R^3$ is independently selected from each occurrence from the groups consisting of hydrogen substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl, —C(O) attached to a $C_1$-$C_6$ substituted or unsubstituted alkyl; comprising the steps of:

a) reacting a compound of the Formula XX:

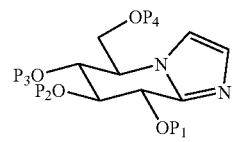

wherein $P_1$, $P_2$, $P_3$ and $P_4$ are O-protection groups, with N-iodo-succinimide in a polar aprotic solvent or additional reactions for selective removal of 3-iodo group from Formula XXII to afford compounds of the Formula XXI, XXII, or XXIII:

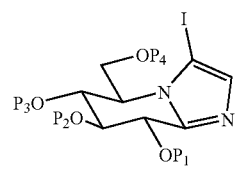

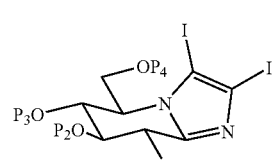

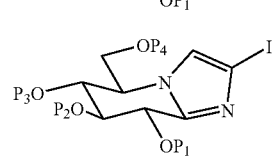

b) reacting a compound of the Formula XXI, XXII or XXIII with a compound of the Formula XXIV or XXV:

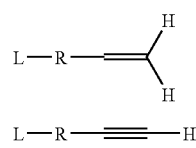

wherein L is a $L^1$ or $L^2$ and R is $R^1$ or $R^2$, in the presence of Palladium catalyst such as $Pd(PPh_3)_4$ in a polar aprotic solvent to afford a compound of the Formula XXVI:

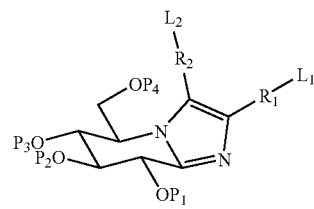

and;

c) deprotection of O-protection groups affords formula XV:

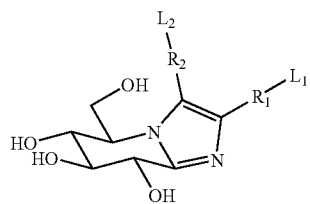

Therapeutic Applications

The present invention further provides a method for the prevention or treatment of Gaucher disease, which method comprises increasing the expression or activity of the mutant GCase, or by increasing or stabilizing the activity of recombinant, wild-type replacement GCase (i.e., ERT or gene therapy), in a subject or patient in need of such treatment.

According to the present invention, a "therapeutically effective amount" also means an amount of the HP derivative that enhances without inhibiting the activity of the GCase protein, i.e., an effective amount enhances more than it inhibits so the net effect is an enhancement. This will generally fall somewhere below the $IC_{50}$ value of that inhibitor for GCase intracellularly, or below about 50 μM in culture medium.

The small molecule analogue that increases GCase expression or activity is advantageously formulated in a pharmaceutical composition, with a pharmaceutically acceptable carrier. In this context, the HP derivative is the active ingredient or therapeutic agent.

The concentration or amount of the active ingredient depends on the desired dosage and administration regimen, as discussed below. Suitable dose ranges of the small molecule analogue may include from about 10 μg/kg to about 100 mg/kg of body weight per day.

Combination Therapy

HP chaperones and protein replacement. The pharmaceutical compositions of the invention may also include other biologically active compounds in addition to HP derivative of the present invention. For example, in one embodiment, the small molecule may be administered in solution with the replacement, wild-type (or otherwise functional) recombinant GCase during enzyme infusion in replacement therapy. Protein replacement therapy increases the amount of protein by exogenously introducing wild-type or biologically functional protein by way of infusion. This therapy has been developed for many genetic disorders including Gaucher disease. The wild-type enzyme is purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al.; and U.S. Pat. No. 5,879,680 to Ginns et al.), human placenta, or animal milk (see U.S. Pat. No. 6,188,045 to Reuser et al.).

After the infusion, the exogenous GCase is expected to be taken up by tissues through non-specific or receptor-specific mechanism. In general, the uptake efficiency is not high, and the circulation time of the exogenous protein is short. In addition, the exogenous GCase is unstable and subject to rapid intracellular degradation. Accordingly, it is expected that co-administration with the HPcompounds of the present invention, which act as chaperones for the enzyme, will improve the stability and prevent the degradation of the exogenously administered GCase.

In another embodiment, the small molecule analogue also may be administered in conjunction with, but not necessarily the same composition, as the recombinant wild-type, or otherwise functional, GCase protein. In this embodiment, the replacement GCase protein and the HPcompounds of the present invention are formulated in separate compositions. The HP derivative and the replacement GCase may be administered according to the same route, e.g., intravenous infusion, or different routes, e.g., intravenous infusion for the replacement protein, and oral administration for the HPcompound.

HP Derivatives and Gene Therapy. In addition, the HP compositions of the present invention may be administered in conjunction with a recombinant vector encoding a wild-type, or otherwise functional GCase gene, i.e., in association with gene therapy. Recently, recombinant gene therapy methods are in clinical or pre-clinical development for the treatment of lysosomal storage disorders, see, e.g., U.S. Pat. No. 5,658, 567, for recombinant alpha-galactosidase A therapy for Fabry disease; U.S. Pat. No. 5,580,757, for Cloning and Expression of Biologically Active α-galactosidase A as a Fusion Protein; U.S. Pat. No. 6,066,626, for Compositions and method for treating lysosomal storage disease; U.S. Pat. No. 6,083,725, for Transfected human cells expressing human alpha-galactosidase A protein; U.S. Pat. No. 6,335,011, for Methods for delivering DNA to muscle cells using recombinant adeno-associated virus virions to treat lysosomal storage disease; Bishop, D. F. et al., Proc. Natl. Acad Sci. USA 1986; 83:4859-4863; Medin, J. A. et al., Proc. Natl. Acad. Sci. USA 1996; 93:7917-7922; Novo, F. J., Gene Therapy 1997; 4:488-492,; Ohshima, T. et al., Proc. Natl. Acad. Sci. USA 1997; 94:2540-2544; Sugimoto Y. et al., Human Gene Therapy 1995; 6:905-915; Sly et al., Proc. Natl. Acad. Sci. USA 2002;99(9):5760-2; Raben et al., Curr. Mol. Med 2002; 2(2):145-66; Eto et al., Curr. Mol. Med. 2002; 2(1):83-9; Vogler et al., Pediatr. Dev. Pathol. 2001; 4(5):421-33; Barranger et al., Expert Opin. Biol. Ther. 2001; 1(5):857-67; Yew et al., Curr. Opin. Mol. Ther. 2001; 3(4):399-406; Caillaud et al., Biomed. Pharmacother. 2000; 54(10):505-12 and Ioannu et al., J. Am. Soc. Nephrol. 2000; 11(8):1542-7.

It is important to note that in addition to stabilizing the expressed GCase enzyme, the HP derivative will also stabilize and enhance expression of any endogenous mutant GCase that is deficient as a result of mutations that prevent proper folding and processing in the ER.

Formulations and Administration

According to the invention, the pharmaceutical composition of the invention, e.g., the HP derivative, can be introduced parenterally, transmucosally, e.g., orally (per os), nasally, or rectally, or transdermally. Parental routes include intravenous, intra-arteriole, intramuscular, intradermal, subcutaneous, intraperitoneal, intraventricular, and intracranial administration.

With respect to combination therapy with protein replacement, in the embodiment where the HP derivative is administered in the same composition with the replacement GCase enzyme, the formulation is preferably suitable for parenteral administration, including intravenous subcutaneous, and intraperitoneal, however, formulations suitable for other routes of administration such as oral, intranasal, or transdermal are also contemplated.

In one embodiment, transdermal administration is achieved by liposomes. Lipid bilayer vesicles are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants such as alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into Unilamellar Vesicles (UV) with the application of a shearing force.

The pharmaceutical formulations suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, and sorbic acid. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin. The advantage of using liposomes to deliver the ceramide and sphyingomyelin analogues according to the method of the present invention is that liposomes cross the blood-brain barrier. Since Types 2 and 3 Gaucher disease are characterized by neurodegeneration due to an accumulation of glucoceramide, effective targeting to the brain is critical for any therapeutic.

Sterile injectable solutions are prepared by incorporating the purified GCase and HP derivative in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation contains an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation also preferably contains a non-ionic detergent. Preferred non-ionic detergents include Polysorbate 20, Polysorbate 80, Triton X-100, Triton X-114, Nonidet P-40, octyl α-glucoside, octyl β-glucoside, Brij 35, Pluronic, and Tween 20.

For lyophilization of GCase and HP preparations, the enzyme concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

Formulations of HP compound (with or without the GCase) for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 gram per cubic centimeter and mean diameters exceeding 5 μm efficiently deliver inhaled therapeutics into the systemic circulation. Such particles are inspired deep into the lungs and escape the lungs' natural clearance mechanisms until the inhaled particles deliver their therapeutic payload (Edwards et al., Science 1997; 276:1868-1872). Replacement protein preparations of the present invention can be administered in aerosolized form, for example by using methods of preparation and formulations as described in, U.S. Pat. Nos. 5,654,007, 5,780,014, and 5,814,607, each incorporated herein by reference. Formulation for intranasal administration may include oily solutions for administration in the form of nasal drops, or as a gel to be applied intranasally.

Formulations for topical administration to the skin surface may be prepared by dispersing the composition with a dermatological acceptable carrier such as a lotion, cream, ointment, or soap. Particularly useful are carriers capable of forming a film or layer over the skin to localize application and inhibit removal. For topical administration to internal tissue surfaces, the composition may be dispersed in a liquid tissue adhesive or other substance known to enhance adsorption to a tissue surface. Alternatively, tissue-coating solutions, such as pectin-containing formulations may be used.

In preferred embodiments, the formulations of the invention are supplied in either liquid or powdered formulations in devices which conveniently administer a predetermined dose of the preparation; examples of such devices include a needleless injector for either subcutaneous or intramuscular injection, and a metered aerosol delivery device. In other instances, the preparation may be supplied in a form suitable for sustained release, such as in a patch or dressing to be applied to the skin for transdermal administration, or via erodable devices for transmucosal administration. In instances where the formulation, e.g., the HP is orally administered in tablet or capsule form, the preparation might be supplied in a bottle with a removable cover or as blister patches.

In the embodiment where the HP derivative is administered separately than the GCase (or a vector comprising a GCase gene), is administered alone as monotherapy, the compound can be in a form suitable for any route of administration, including but not limited to all of the forms described above. Alternatively, in a preferred embodiment, the small molecule analogue can be formulated for oral administration in the form of tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration of HP derivative may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

The small molecule analogue may also be formulated in rectal compositions such as suppositories or retention enemas, e.g., containing conventional suppository bases such as cocoa butter or other glycerides.

In addition to the formulations described above, the HP derivative may also be formulated as a depot preparation. Such long acting formulations may be administered by implantation (for example subcutaneously or intramuscularly) or by intramuscular injection. Thus, for example, the HP derivative may be formulated with suitable polymeric or hydrophobic materials (for example as an emulsion in an acceptable oil) or ion exchange resins, or as sparingly soluble derivatives, for example, as a sparingly soluble salt.

Timing. When the replacement GCase protein and HP derivative are in separate formulations, administration may be simultaneous, or the HP derivative may be administered prior to, or after the GCase replacement protein. For example, where the replacement protein is administered intravenously, the HP derivative may be administered during a period from 0 h to 6 h later. Alternatively, the HP derivative may be administered from 0 to 6 h prior to the protein.

In a preferred embodiment, where the HP derivative and replacement protein are administered separately, and where the has a short circulating half-life (e.g., small molecule), the HP derivative may be orally administered continuously, such as daily, in order to maintain a constant level in the circulation. Such constant level will be one that has been determined to be non-toxic to the patient, and optimal regarding interaction with a target replacement protein during the time of administration to confer a non-inhibitory, therapeutic effect.

In another embodiment, the HP derivative is administered during the time period required for turnover of the replacement GCase protein (which will be extended by administration of the small molecule analogue).

Regardless of the timing, the administration must be such that the concentrations of the GCase and HP derivative must be such that the small molecule stabilizes, but does not prevent or inhibit the protein's activity in vivo. This also applies where the replacement protein and small molecule are administered in the same formulation.

With respect to the timing of the HP derivative and gene therapy combination therapy, administration of the small molecule according to the present invention will generally follow delivery of the GCase gene, to allow for expression of the recombinant enzyme by the target cells/tissue. Since the expression of the GCase gene will be sustained for a period of time, for as long as the gene is expressible, the HP derivative will be remained effective as a chaperone and stabilizer for the recombinant enzyme. Therefore, administration of the chaperone molecule will be necessary for the same period as the gene is expressed.

In a preferred embodiment, since the HP derivative may have a short circulating half-life, it is preferred that it will be orally administered frequently, such as daily, in order to maintain a constant level in the circulation. Such a constant level will be one that has been determined to be non-toxic to the patient, and optimal regarding interaction with the protein, which will be continuously produced, to confer a non-inhibitory, therapeutic effect.

According to the present invention, since that the therapeutic GCase gene supplements inadequate activity of an endogenous mutant GCase gene, the timing of the small molecule analogue delivery becomes less significant since the effective amount can enhance the activity of the endogenous mutant GCase as well as increase the efficiency of the therapeutic GCase gene product.

The presence of an small molecule chaperone, e.g., the HP derivative of the present invention, for the GCase encoded by the administered GCase gene will have the benefit of improving the efficiency of protein processing during synthesis in the ER (i.e., by preventing aggregation), and prolonging in the circulation and tissue the half-life of the GCase, thereby maintaining effective levels over longer time periods. This will result in increased expression in clinically affected tissues. This confers such beneficial effects to the Gaucher patient as enhanced relief, reduction in the frequency of treatment, and/or reduction in the amount of GCase gene administered. This will also reduce the cost of treatment.

Dosages

The amount of the HP compound effective to stabilize the administered GCase protein and/or endogenous GCase mutant protein can be determined by those skilled in the art. Pharmacokinetics and pharmacodynamics such as half-life ($t_{1/2}$), peak plasma concentration ($C_{max}$), time to peak plasma concentration ($t_{max}$), exposure as measured by area under the curve (AUC), and tissue distribution for both the replacement GCase protein and the small molecule analogue as well as data for the small molecule analogue-replacement GCase protein binding (affinity constants, association and dissociation constants, and valency), can be obtained using ordinary methods known in the art to determine compatible amounts required to stabilize the replacement GCase protein, without inhibiting its activity, and thus confer a therapeutic effect.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

The particular dosage used in any treatment may vary within this range, depending upon factors such as the particular dosage form employed, the route of administration utilized, the conditions of the individual (e.g., patient), and so forth.

According to current methods, the concentration of replacement GCase protein is between 0.05-5.0 mg/kg of body weight, typically administered weekly or biweekly. The protein can be administered at a dosage ranging from 0.1 μg/kg to about 10 mg/kg, preferably from about 0.1 mg/kg to about 2 mg/kg. Regularly repeated doses of the protein are necessary over the life of the patient. Subcutaneous injections maintain longer term systemic exposure to the drug. The GCase is preferably administered intravenously, e.g., in an intravenous bolus injection, in a slow push intravenous injection, or by continuous intravenous injection. Continuous IV infusion (e.g., over 2-6 hours) allows the maintenance of specific levels in the blood.

The optimal concentrations of the HP derivative will be determined according to the amount required to stabilize the recombinant GCase protein in vivo, in tissue or circulation, without preventing its activity, bioavailability of the small molecule analogue in tissue or in circulation, and metabolism of the small molecule analogue in tissue or in circulation. For example, the concentration of the C-nonyl-HP may be determined by calculating the $IC_{50}$ value of the C-nonyl-HP for GCase. Taking into consideration bioavailability and metabolism of the compound, concentrations around the $IC_{50}$ value or slightly over the $IC_{50}$ value can then be evaluated based on effects on GCase activity, e.g., the amount of small molecule analogue needed to increase the amount of GCase activity or prolong activity of replacement GCase.

EXAMPLES CL Example 1

Synthesis of 6-alkyl-hydroxypiperidines a. Benzyl α-L-(+)-xylopyranoside

L(−)-xylose (5.0 g, 33.3 mmol) is combined with 25 ml benzyl alcohol and treated with 1 ml of acetyl chloride. The resulting mixture is warmed to 50° C. and stirred for 24 hrs. After cooling to room temperature, 80 ml of tert-butyl methyl ether is added and the mixture is kept at 5° C. for 24 h. The crystals that form are collected and washed with ice-cold tert-butyl ether to give the title compound as the α-anomer. m.p. 120° C. $^1$H NMR (400 MHz, DMSO-$d_6$): δ7.40-7.28 (m, 5H), 4.93 (d, 1H, J=4.8 Hz), 4.71 (d, 1H, J=3.6 Hz), 4.82-4.78 (m, 2H), 4.65 (d, 1H, J=12.4 Hz), 4.44 (d, 1H, J=12 Hz), 3.47-3.38 (m, 2H), 3.36-3.27 (m, 3H), 3.25-3.21 (m, 1H). MS: 258 [M+$NH_4^+$].

b. Benzyl 2,3-isopropylidene-L-xylopyranoside

A mixture of benzyl α-L-xylopyranoside (15 g, 62.5 mmol), 2-methoxypropene (15 ml, 156.6 mmol) and p-toluenesulfonic acid monohydrate (300 mg, 1.6 mmol) are dissolved in anhydrous THF and stirred at 0° C. for 1.5 hrs. Triethylamine (1 ml) is added and stirring is continued for 10 min. The reaction mixture is diluted with ethyl acetate (400 ml), washed with sat. aq. NaCl, ice water, and the organic layer dried over $Na_2SO_4$. After filtration, the solution is concentrated using a rotovap and the crude product is purified using a flash chromatography column eluted with heptane/EtOAc (4:1). The title compound is isolated as a colorless syrup. $^1$H NMR (400 MHz, $CDCl_3$): δ7.27-7.20 (m, 5H), 5.10 (d, 1H, J=2.4 Hz), 4.70 (d, 1H, J=12 Hz), 4.53 (d, J=12 Hz), 3.92-3.88 (m, 2H), 3.65 (dd, 1H, J=4.8 Hz and 11.6 Hz), 3.38-3.36 (m, 1H), 3.27 (t, 1H, J=9.6 Hz), 1.38 (s, 3H), 1.35 (s, 3H). MS (ES+): 281 [M+1].

c. Benzyl 4-cyano-4-deoxy-2,3-O-isopropylidene-L-xylopyranoside

Benzyl 2,3-isopropylidene-L-xylopyranoside (4 g, 14.3 mmol) and pyridine (3.8 ml) are dissolved in 50 ml of $CH_2Cl_2$, stirred and cooled to −78° C. Trifluoromethanesulfonic anhydride (3.2 ml, 19 mmol) is slowly added and the reaction mixture stirred for 1.5 hrs, then at warmed 0° C. for an additional 2 hrs. EtOAc (500 ml) is added and the organic solution is washed successively with saturated aqueous NaCl and ice water. The organic phase is dried ($Na_2SO_4$) and evaporated. Flash chromatography using $CH_2Cl_2$ as an eluant gives the desired triflate. MS (ES+): 413 [M+1]. The above triflate (5.3 g, 12.9 mmol), KCN (9 g, 138 mmol), 18-crown-6 (4 g), and 4A molecular sieves (10 g) are combined and stirred in 300 ml of dry DMF at ambient temperature for 16 hrs. EtOAc (400 ml) is added and the solution is washed successively with sat. aq. NaCl and $H_2O$. The organic phase is dried ($Na_2SO_4$) and evaporated. Flash chromatography ($CH_2Cl_2$) gives the title compound as pale yellow syrup. $^1$H NMR (300 MHz, $CDCl_3$): δ7.28-7.22 (m, 5H), 5.28 (d, 1H, J=3 Hz), 4.69 (d, 1H, J=12 Hz), 4.59 (d, 1H, J=12 Hz), 4.04 (dd, 1H, J=4.8 Hz and 9.6 Hz), 3.87-3.80 (m, 2H), 3.70 (dd, 1H, J=3 Hz and 12 Hz), 3.23-3.21 (m, 1H), 1.42 (s,6H). MS (ES+): 290 [M+1], 307 [M+$NH_4^+$].

d. Benzyl 4-(1-aminopentyl)-4-deoxy-2,3-isopropylidene-L-xylopyranoside

Benzyl 4-cyano-4-deoxy-2,3-O-isopropylidene-L-xylopyranoside (65 mg, 0.225 mmol) is dissolved in 1 ml of anhydrous ether and stirred at room temperature. Butyl-magnesium chloride (0.225 ml of 2 M solution in diethyl ether) is slowly added and the reaction mixture is stirred for 14 h. LiAlH$_4$ (25 mg) is added and the reaction mixture is stirred at ambient temperature for an additional 5 hrs. Water (5 ml) and NaOH (1 N, 5 ml) are added and the mixture is stirred for 30 min. The mixture is transferred to a separatory funnel and extracted with t-butyl methyl ether (2×20 ml). The organic phase is dried and evaporated using a rotovap. The residue is purified by chromatography ($CH_2Cl_2$, and then $CH_2Cl_2$/

MeOH/Et₃N 200:20:1) to give the title compound as yellow syrup. ¹H NMR (400 MHz, CDCl₃): δ 7.35-7.29 (m, 5H), 5.13 (d, 1H, J=2.4 Hz), 4.69 (d, 1H, J=12 Hz), 4.51 (d, 1H, J=12 Hz), 4.06 (t, 1H, J=10.4 Hz), 3.65 (dd, 1H, J=4.8 Hz and 11.6 Hz), 3.63-3.55 (m, 2H), 3.40 (dd, 1H, J=2.8 and 9.6 Hz), 2.96-2.90 (m, 1H), 1.36 (s, 3H), 1.35 (s, 3H), 1.20-1.10 (m, 6H), 0.82 (t, 3H, J=6.8 Hz). MS (ES+): 350 [M+1].

e. Benzyl 4(1-aminodecyl)-4-deoxy-2,3-isopropylidene-L-xylopyranoside

In a similar manner to that described in example 1d, n-C₉H₁₉MgBr is reacted with benzyl 4-cyano-4-deoxy-2,3-O-isopropylidene-L-xylopyranoside to give the title compound. ¹H NMR (300 MHz, CDCl₃): δ 7.35-7.29 (m, 5H), 5.24 (d, 1H, J=2.8 Hz), 4.74 (d, 1H, J=12 Hz), 4.61 (d, 1H, J=12 Hz), 4.31 (dd, 1H, J=5.2 Hz and 10.4 Hz), 3.80 (dd, 1H, J=3.2 Hz and 9.6 Hz), 3.71-3.64 (m, 2H), 3.43-3.40 (m, 1H), 2.41-2.38 (m, 1H), 1.47 (s, 3H), 1.45 (s, 3H), 1.29-1.20 (m, 16H), 0.87 (t, 3H, J=6.4 Hz). MS (ES+): 420 [M+1].

f. Benzyl4-(1-aminooctyl)-4-deoxy-2,3-isopropylidene-L-xylopyranoside

In a similar manner to that described in example 1d, n-C₇H₁₅MgBr is reacted with benzyl 4-cyano-4-deoxy-2,3-O-isopropylidene-L-xylopyranoside to give the title compound. ¹H NMR (400 MHz, CDCl₃): δ 7.20-7.31 (m, 5H), 5.19 (d, 1H, J=₂.0 Hz), 4.69 (d, 1H, J=7.5 Hz), 4.56 (d, 1H, J=7.75 Hz), 4.26 (dd, 1H, J=3.0 Hz and 6.5 Hz), 3.79 (dd, 1H, J=2.0 Hz and 6.25 Hz), 3.65-3.58 (m, 2H), 3.24-3.20 (m, 1H), 2.22-2.15 (m, 1H), 1.40 (s, 6H), 1.23-1.15 (m, 12 H), 0.9 (t, 3H, J=6.4 Hz); MS (ES+): 329 [M+1].

g. Benzyl-4-(1-anminoheptyl)-4-deoxy-2,3-isopropylidene-L-xylopyranoside

In a similar manner to that described in example 1d, n-C₆H₁₃MgBr is reacted with benzyl 4-cyano-4-deoxy-2,3-O-isopropylidene-L-xylopyranoside to give the title compound. ¹H NMR (400 MHz, CDCl₃): δ 7.30-7.20 (m, 5H), 4.85 (d, 1H, J=11.2 Hz), 4.65 (d, 1H, J=1.6 Hz), 4.55 (d, 1H, J=11.2 Hz), 4.30 (t, 1H, J=3.6), 4.09 (dd, 1H, J=4.8 Hz and 11.6 Hz), 3.94 (dd, 1H, J=2.4 Hz and 12.8 Hz), 3.86 (dd, 1H, J=1.6 Hz and 4.0 Hz), 3.75 (m, 1H), 2.71-2.80 (m, 1H), 1.40-1.21 (m, 16H), 0.83 (t, 3H, J=6.4 Hz). MS (ES+): 378 [M+1].

h. Benzyl4-(1-aminononyl)-4-deoxy-2,3-isopropylidene-L-xylopyranoside

In a similar manner to that described in example 1d, n-C₈H₁₇MgBr is reacted with benzyl 4-cyano-4-deoxy-2,3-O-isopropylidene-L-xylopyranoside to give the title compound. ¹H NMR (400 MHz, CDCl₃): δ 7.30-7.20 m, 5H), 5.20 (d, 1H, J=2.0 Hz), 4.70 (d, 1H, J=8.0 Hz), 4.50 (d, 1H, J-8.0 Hz), 4.25 (dd, 1H, J=4.0 Hz and 8.0 Hz), 3.74 (dd, 1H, J=3.1 Hz and 9.3 Hz), 3.65-3.50 (m, 2H), 3.25-3.15 (m, 1H), 2.20-2.10 (m, 1H), 1.40 (s, 6H), 1.25-1.15 (m, 14H), 0.80 (t, 3H, J=6.3 Hz); MS(ES+): 406 [M+1].

i. Benzyl4-(1-amino-2-phenylethyl)-4-deoxy-2,3-isopropylidene-L-xylopyranoside

In a similar manner to that described in example 1d, PhCH₂MgCl is reacted with benzyl 4-cyano-4-deoxy-2,3-O-isopropylidene-L-xylopyranoside to give the title compound. ¹H NMR (300 MHz, CDCl₃): δ 7.38-7.26 (m, 10H), 5.24 (d, 1H, J=2.8 Hz), 4.78 (d, 1H, J=13.7 Hz), 4.64 (d, 1H, J=13.3 Hz), 4.34 (dd, 1H, J=5.6 Hz and 11.6 Hz), 3.88 (m, 2H), 3.75 (dd, 1H, J=3.3 Hz and 14.3 Hz), 3.55-3.46 (m, 1H), 3.09 (dd, 1H, J=3.0 Hz and 14.3 Hz), 2.41 (dd, 1H, J=11.3 Hz and 14.4 Hz), 2.21 (m, 1H), 2.13 (s, 2H), 1.45 (s, 3H), 1.40 (s, 3H); MS(ES+): 384[M+1].

j. (3R, 4R, 5R, 6S)-5-(Hydroxymethyl)-6-n-butyl-3,4-dihydroxypiperidine

Benzyl 4-(1-aminopentyl)-4-deoxy-2,3-isopropylidene-L-xylopyranoside (27 mg) is dissolved in 2 ml of methanol and stirred. Pd(OH)₂ (22 mg of 20 wt % on carbon) is added followed by 1 drop of conc. HCl (conc. 1 drop) The mixture is rapidly stirred under an atmosphere of H₂ for 24 h. The reaction mixture is filtered through Celite and the filtrate concentrated using a rotovap. The crude product is purified by chromatography using Amberlite CG-50 ion-exchange resin (NH₄⁺ form), eluted with 0.1N aqueous NH₄OH, to give the title compound. ¹H NMR (400 MHz, D₂O): 3.91 (d, 1H, J=11.6 Hz), 3.79 (d, 1H, J=12 Hz), 3.50-3.43 (m, 2H), 3.11 (dd, 1H, J=2.8 and 10.5 Hz), 2.61 (t, 1H, 9.6 Hz), 2.41 (t, 1H, J=10 Hz), 1.73-1.71 (m, 1H), 1.43-1.21 (m, 6H), 0.90 (t, 3H, J=6.4 Hz). MS (ES+): 204 [M+1].

k. (3R, 4R, 5R, 6S)-5-(Hydroxymethyl)-6-n-heptyl-3,4-dihydroxypiperidine

In a similar manner to that described in Example 1j, benzyl 4-(1-aminooctyl)-4-deoxy-2,3-isopropylidene-L-xylopyranoside is converted to the title compound. ¹H NMR (400 MHz, CD₃OD): δ 3.96 (dd, 1H, J=1.5 Hz and 7.3 Hz), 3.63 (dd, 1H, J=1.8 Hz and 7.3 Hz), 3.45-3.10 (m, 2H), 3.35-3.20 (m, 2H), 3.00-2.95 (m, 1H), 2.65 (t, 1H, J=14.8 Hz), 1.90-1.81 (m, 1H), 1.60-1.25 (m, 14H), 0.90 (t, 3H, J=6.5 Hz); MS(ES+): 246 [M+1].

l. (3R, 4R, 5R, 6S)-5-(Hydroxymethyl)-6-n-hexyl-3,4-dihydroxypiperidine

In a similar manner to that described in Example 1j, benzyl 4-(1-aminoheptyl)-4-deoxy-2,3-isopropylidene-L-xylopyranoside is converted to the title compound. ¹H NMR (300 MHz, CD₃OD): δ 3.95 (dd, 1H, J=2.4 Hz and 11.4 Hz), 3.68 (dd, 1H, J=3.0 Hz and 11.4 Hz), 3.49-3.43 (m, 2H), 3.16 (dd, 1H, J=4.2 Hz and 12 Hz), 2.83-2.76 (m, 1H), 2.51 (dd, 1H, J=10.8 Hz and 12.7 Hz), 1.79-1.75 (m, 1H), 1.46-1.26 (m, 10H), 0.90 (t, 3H, J=6.6 Hz); MS (ES+): 232 [M+1], 254 [M+Na].

m. (3R, 4R, 5R, 6S)-5-(Hydroxymethyl)-6-n-octyl-3,4-dihydroxypiperidine

In a similar manner to that described in Example 1j, benzyl 4-(1-aminononyl)4-deoxy-2,3-isopropylidene-L(?)-xylopyranoside is converted to the title compound. ¹H NMR (400 MHz, CD₃OD): δ 4.11 (dd, 1H, J=1.3 Hz and 7.3 Hz), 3.79-3.69 (m, 2H), 3.62 (t, 1H, J=12.0 Hz), 3.43 (dd, 1H, J=3.3 Hz and 7.8 Hz), 3.36-3.31 (m, 1H), 2.88 (t, 1H, J=15.0 Hz), 2.06-1.98 (m, 1H), 1.74-1.7-(m, 1H), 1.45-1.40 (m, 14H), 0.99 (t, 3H, J=8.5 Hz); MS(ES+): 260 [M+1].

n. (3R, 4R, 5R, 6S)-5-(Hydroxymethyl)-6-benzyl-3,4-dihydroxypiperidine

In a similar manner to that described in Example 1j, benzyl 4-(1-amino-2-phenylethyl)4deoxy-2,3-isopropylidene-L-xylopyranoside is converted to the title compound. ¹H NMR (400 MHz, CD₃OD): δ 7.42-7.31 (m, 5H), 4.12 (dd, 1H, J=1.3 Hz and 7.5 Hz), 3.88 (dd, 1H, J=2.0 Hz and 7.3 Hz), 3.73-3.66 (m, 1H), 3.58-3.53 (m, 2H), 3.49 (dd, 1H, J=2.3 Hz and 9.3 Hz), 3.26 (dd, 1H, J=2.5 Hz and 13.5 Hz), 2.79 (dd, 1H, J=5.3 Hz and 10.0 Hz), 2.68 (t, 1H, J=15.0 Hz), 1.68 (m, 1H); MS(ES+): 238 [M+1].

o. (3R, 4R, 5R, 6S)-5-(Hydroxymethyl)-6-n-nonyl-3,4-dihydroxypiperidine

Benzyl 4-(1-aminodecyl)-4-deoxy-2,3-O-isopropylidene-α-L-xylopyranoside (55 mg) is dissolved in THF (2 ml) and hydrogenated over 20% Pd(OH)₂/C (52 mg) at atmospheric pressure for 21 h. The reaction mixture is filtered and concentrated to give the isopropylidene protected product (31 mg) as a pale yellow syrup. The syrup (13 mg) is treated with 1N HCl (2 ml) overnight. The solvent is removed under vacuum and residue is purified by solid phase extraction using a C-18 cartridge. The residue is lyophilized from water (0.5 ml) to afford the title compound as white foam. $^1$H NMR (400 MHz, CD$_3$OD): δ 3.94 (dd, 1H, J=2.1 Hz and 11.4 Hz), 3.60 (dd, 1H, J=2.8 Hz and 11.4 Hz), 3.58-3.51 (m, 1H), 3.45 (t, 1H, J=9 Hz), 3.26 (dd, 1H, J=4.8 and 12.4 Hz), 3.22-3.14 (m, 1H), 2.71 (t, 1H, J=11.6 Hz), 1.88-1.81 (m, 1H), 1.47-1.22 (m, 16H), 0.82 (t, 3H, J=6.4 Hz). MS (ES+): 274 [M+1]. CL Example 2

Synthesis of 6-alkyl-hydroxypiperidines Using a Linker Strategy a. Benzyl 4-(1-aminobut-3-enyl)-4-deoxy-2,3-isopropylidene-L-xylopyranoside Benzyl 4-cyano-4-deoxy-2,3-O-isopropylidene-L(−)-xylopyranoside (1.67 g, 5.79 mmol) is dissolved in 40 ml of anhydrous ether and stirred at room temperature. allylmagnesium bromide (23 ml of 1 M solution in diethyl ether) is added dropwise and the reaction mixture is stirred for 5 h. NaBH$_4$ (1.75 g) is added and the reaction mixture is stirred at ambient temperature overnight. Cooled with ice bath, Methanol (10 ml) and water (10 ml) are dropwise added and the mixture is stirred for 30 min. t-Butyl methyl ether (100 ml) is added and solid was filtered off. The filtrate is transferred to a separatory funnel and washed with water (2×20 ml). The organic phase is dried and evaporated using a rotovap. The residue is purified by chromatography (CH$_2$Cl$_2$/EtOAc 10:1 and then CH$_2$Cl$_2$/MeOH 15:1) to give the title compound (0.674 g, 35%) as pale yellow syrup. $^1$H NMR (400 MHz, CDCl$_3$): δ 7.37-7.26 (m, 5H), 5.84-5.77 (m, 1H), 5.24 (d, 1H, J=3.3 Hz), 5.14-5.08 (m, 2H), 4.75 (d, 1H, J=12 Hz), 4.60 (d, 1H, J=12 Hz), 4.30 (dd, 1H, J=4.8 Hz and 10.2 Hz), 3.86 (dd, 1H, J=3.3 Hz and 9.9 Hz), 3.76-3.65 (m, 2H), 3.36-3.29 (m, 1H), 2.49-2.41 (m, 1H), 2.11-1.89 (m, 2H), 1.45 (s, 6H). MS (ES+): 334 [M+1].

b. (3R, 4R, 5R, 6S)-6-[(1,3-dioxolan-2-yl)methyl]-5-(Hydroxymethyl)-3,4-isopropylidenedioxy Piperidine Benzyl 4-(1-aminobut-3-enyl)-4-deoxy-2,3-isopropylidene-L-xylopyranoside is treated with benzyl chloroformate, and then ozonolysis of terminal alkene is carried out to generate an aldehyde. Condensation of aldehyde with ethylene glycol gives 1,3-dioxolane. Further hydrogenation generates the titled compound.

c. 2-[(2S, 3R, 4R, 5R)-1-benzyl4,5-bis(benzyloxy)-3-(benzyloxymethyl) piperidine-2-yl]acetaldehyde (3R, 4R, 5R, 6S)-6-[(1,3-dioxolan-2-yl)methyl]-5-(Hydroxymethyl)-3,4-isopropylidenedioxy piperidine is treated with aqueous acetic acid to selectively cleave the acetonide. Following the treatment with benzyl bromide, fully benzyl protected product will be formed. 1,3-dioxolane can be further cleaved by trifluoroacetic acid to give the titled compound.

d. (3R, 4R, 5R, 6S)-1-6-[2-(hexylamino)ethyl] -5-(hydroxymethyl)piperidine3,4diol Reaction of 2-[(2S, 3R, 4R, 5R)-1-benzyl-4,5-bis(benzyloxy)-3-(benzyloxymethyl) piperidine-2-yl] acetaldehyde with hexylamine in the presence of NaBH$_3$CN and then catalytic hydrogenation to remove benzyl group will give the titled compound. CL Example 3

Inhibitory Activity of 6-nonyl HP Against GCase

Methods. The enzyme activity was assayed with 4-methylumbelliferyl β- glucoside (final concentration 3 mM) as substrate in Reaction Buffer consisting 0.25% sodium taurocholate, 0.1% Triton X-100 in McIlvaine buffer (0.1M citrate and 0.2M phosphate buffer) at pH 5.2. The compounds were added to each reaction mixture individually at the final concentration indicated. After incubation with the diluted human GCase at 37° C. for 30 min, the reaction was stopped by addition of 0.2 M glycine buffer, pH 10.8, the released 4-methylumbelliferone was determined by a fluoremeter at excitation wavelength of 355 nm and emission wavelength at 460 nm, respectively. The relative enzyme activity was calculated as a percentage to those of reactions without inhibitors. IC$_{50}$ was calculated using Prism sigmoid plot.

Figure 2:
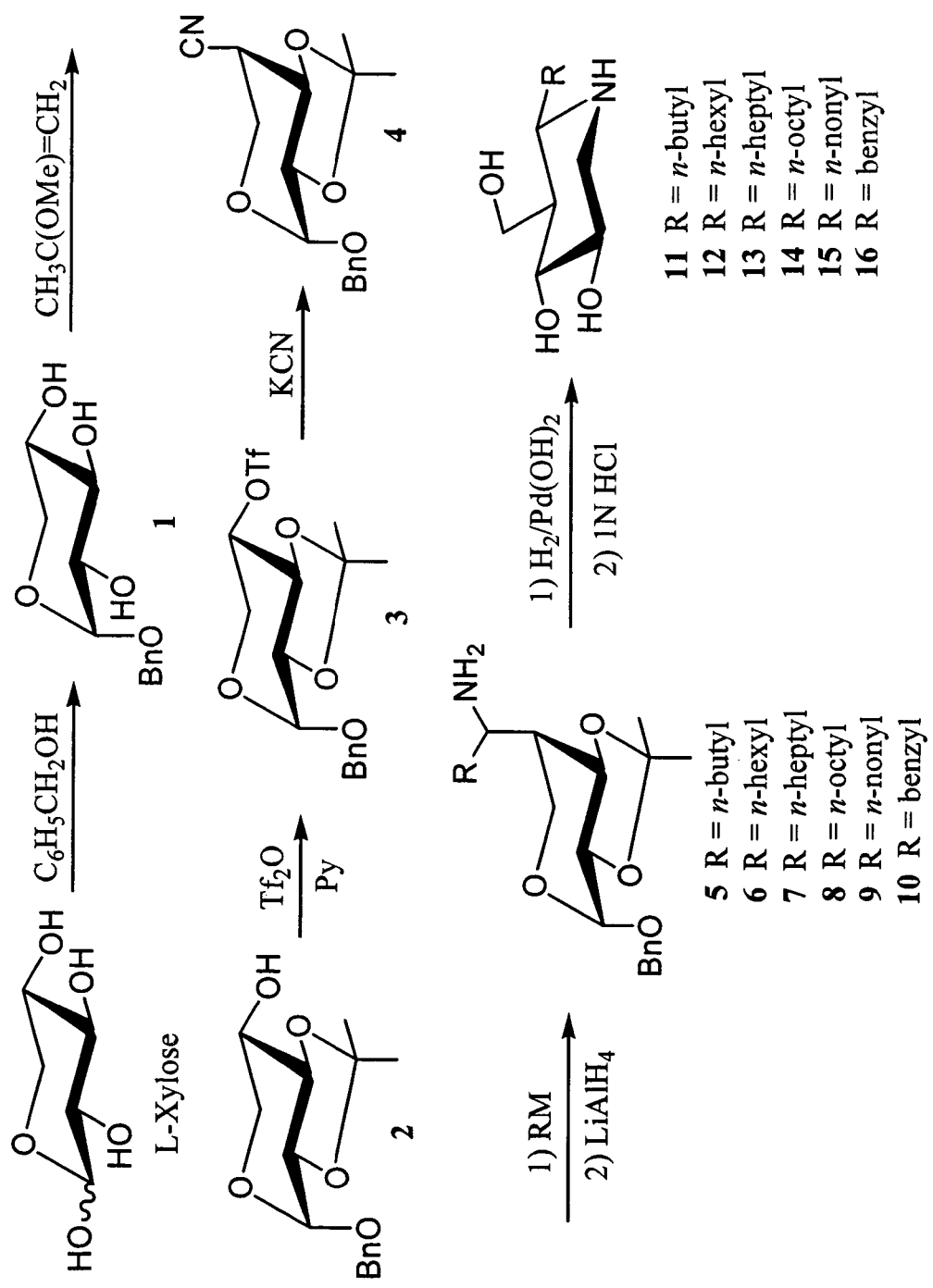
FIG. 2. Synthesis of 6-alkyl derivatives of HP. L-xylose is converted to α-benzyl xyloside (1) by stirring with benzyl alcohol at 50° C. in the presence of acid and then crystallizing the alpha-anomer from tert-butyl methyl ether at 0° C. The 2,3-O-isopropylidene derivative of benzyl α-xyloside is formed by acid-catalysed trans-acetalation of 2-methoxypropene in THF. Conversion of the remaining free 4-hydroxy group to the corresponding trifluoromethane sulfonate of protected benzyl α-xyloside acetonide (2) gives compound 3 in synthetically useful yields. Subsequent treatment with potassium cyanide and 18-crown-6 in anhydrous DMF leads to the nitrile (4). Addition of organometallic compounds, such as Grignard reagents, to the nitrile followed by reduction of the intermediate imine affords amines (5-10). Hydrogenolysis of compound 5-10 in the presence of Pd(OH)$_2$/C, followed by deprotection of isopropylidene group, gives the respective 6-alkyl HP derivatives.
Figure 3:
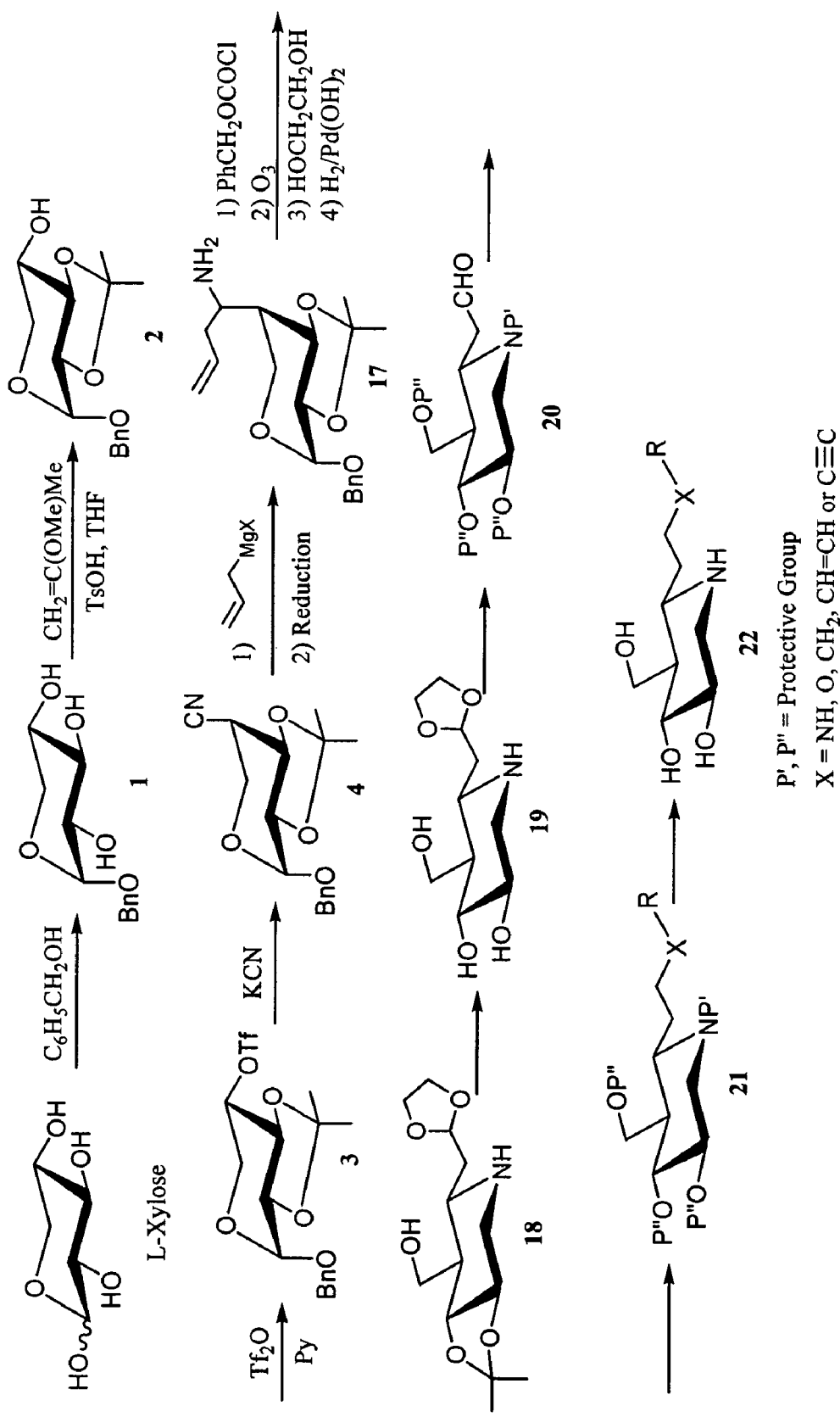
FIG. 3. Alternative synthesis of 6-derivatives of HP. Compound 4 is prepared as described above. Addition of Grignard reagent (allylmagnesium bromide) to nitrile (4), followed by reduction with NaBH$_4$ (alternatively, 1 may be used), gives amine compound (17). Compound 17 is protected with benzyl chloroformate, followed by ozonolysis of terminal alkene, condensation of aldehyde with ethylene glycol and hydrogenation to afford compound 18. Selective deprotection of isopropylidene group with aqueous HOAc solution gives compound 19. Treatment of compound 19 with NaH and then p-methoxybenzylbromide produces N,O-protected compound, followed by hydrolysis with trifluoroacetic acid generates aldehyde (20). Compound 20 can be converted to compound 21 by one of following methods: 1) reaction of compound 20 with amine under reducing condition; 2) reaction of compound 20 with Wittig reagents; or 3) Reduction of compound 20 with reducing reagents, followed by treatment with SOCl$_2$ and nucleophilic reagents. Deprotection of compound 21 gives compound 22.
Figure 4:
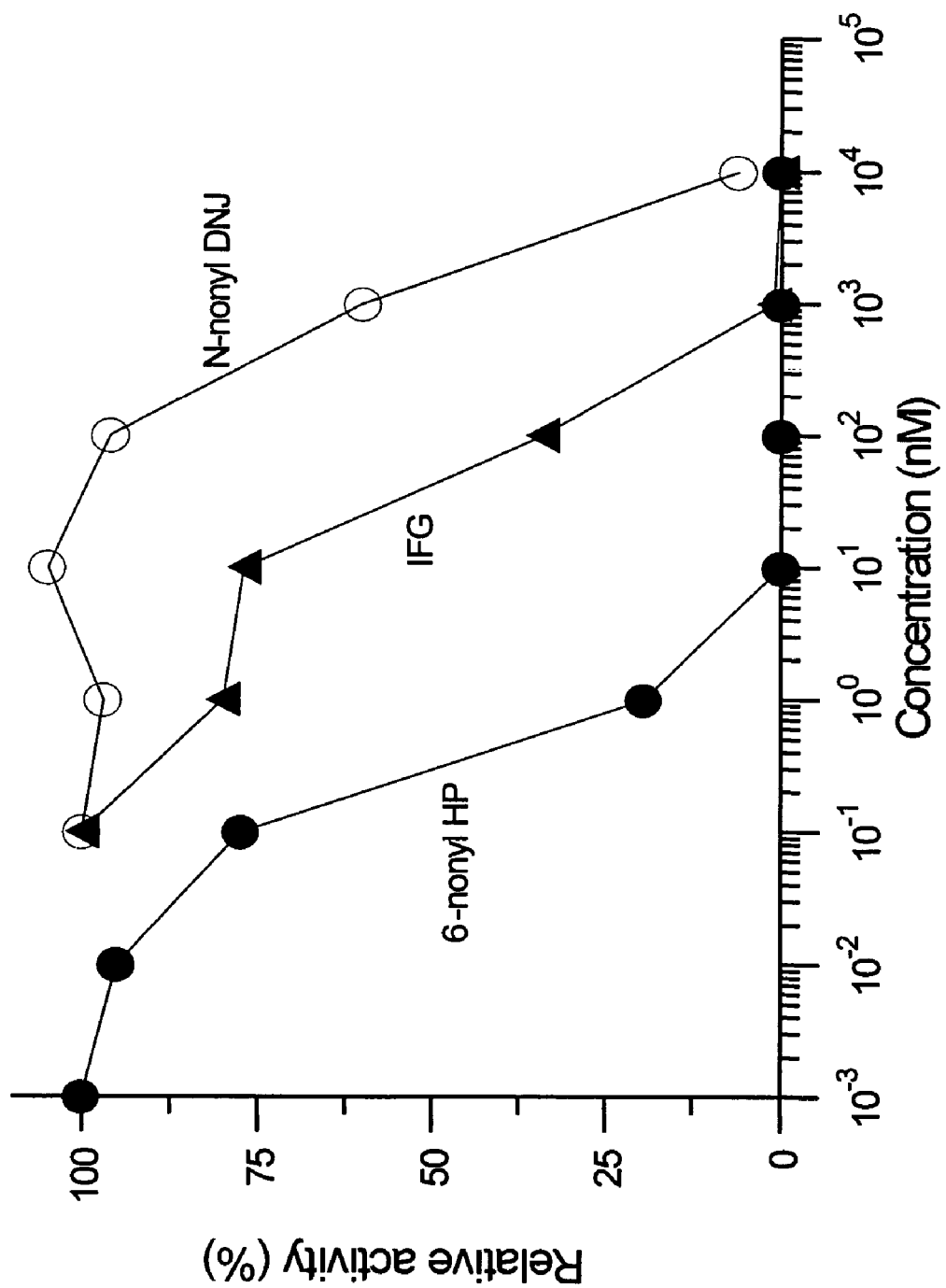
FIG. 4. Inhibitory activity of 6nonyl HP against GCase. The enzyme activity was determined as described in the Examples below. The relative enzyme activity was calculated as a percentage to those of reactions without inhibitors. IC$_{50}$ was calculated using Prism sigmoid plot. ▲=IFG; ○=N-nonyl DNJ; and ●=6-nonyl HP.

Results. The inhibitory activity of 6-alkyl derivatives of HP against human GCase were determined and summarized in Table 1. IFG and N-nonyl DNJ are known potent inhibitors for GCase with IC$_{50}$ values at approximate 50 nM and 2.5 μM, respectively (Fan et al., US1; Sawkar et al., Proc Natl Acad Sci USA., 99:15428-33), which were confirmed (see FIG. 1 for structures). Modification of the imino group with butyl or nonyl chain partially diminished the inhibitory activity (IC$_{50}$ values were 44 μM, or larger), indicating that a positive charge at that position is required for high potency. Addition a butyl group to the 6-C position of the hydroxypiperidine ring, 6-C-butyl hydroxypiperidine (11), did not affect the potency towards GCase. However, 6-C-hexyl hydroxypiperidine (12) was significantly more potent than the IFG, resulting in an approximately 13-fold increase. Further extend the length of the carbon chain improved the potency accordingly (compounds 13-15). Noticeably, to be the best of our knowledge, 6-nonyl hydroxypiperidine (15) is the best inhibitor against human GCase with IC$_{50}$ value at 0.4 nM (FIG. 2). This demonstrates that both a positive charge at the position corresponding to an anomeric carbon of glucose, and a lipophilic moiety extended from the position of the ring oxygen of glucose play an important role in the inhibition of GCase. Since short alkyl chains (C=1-4) of N-alkyl derivatives of DNJ did not improve the inhibitory activity for GCase, a lipophilic moiety with a linker (corresponding to the linear length of approximate 6 or more carbons) at that position is expected to be necessary for the extra potency of the inhibitory activity.

TABLE 1

Inhibitory activity against GCase.

| Entry | Inhibitors | IC$_{50}$ (nM)[a] | Ki (nM) |
|---|---|---|---|
|  | hydroxypiperidine | 56 | 25 |
| 11 | 6-C-butyl hydroxypiperidine | 160 |  |
| 12 | 6-C-hexyl hydroxypiperidine | 4.2 |  |
| 13 | 6-C-heptyl hydroxypiperidine | 1.8 |  |
| 14 | 6-C-octyl hydroxypiperidine | 0.8 |  |
| 15 | 6-C-nonyl hydroxypiperidine | 0.4 |  |
|  | N-butyl hydroxypiperidine | 44,000 |  |
|  | N-nonyl hydroxypiperidine | >100,000 |  |
|  | N-butyl 1-deoxynojirimycin | 270,000 |  |
|  | N-nonyl 1-deoxynojirimycin | 1,800 |  |

[a]All inhibitory activities were determined with 4-methylumbelliferyl β-glucoside at 3 mM concentration.

The X-ray structure of human GCase suggests an annulus of hydrophobic residues surrounds the entrance to the active site (Dvir et al., EMBO reports 2003; 4:1-6). This also reinforces the present discovery that a lipophilic moiety with a short, flexible chain could interact with the hydrophobic amino acid residues at the entrance of the catalytic pocket, and contribute to the inhibitory activity.

Although addition of a shorter alkyl chain to the HP, e.g., 6-butyl HP, does not gain extra potency over HP (or IFG), nevertheless, they are still potent inhibitors of GCase. CL Example 4

Chaperone Activity of 6-nonyl HP for GCase in Gaucher Cells

Methods. Fibroblasts established from Gaucher patients with N370S/N370S mutation were cultured in DMEM medium supplemented with 10% fetal bovine serum and antibiotics at 37° C. under 5% $CO_2$. The C-nonyl HP or IFG was added into the culture medium at the final concentrations as indicated for 4 days prior to the assay. After washing the cells with phosphate-buffered saline, the cells were harvested and homogenized in the presence of 0.25% (w/v) sodium taurocholate and 0.1% (v/v) Triton X-100 in McIlvaine buffer (pH 5.2, Reaction Buffer), and 10 μl of the lysate was used for the determination of residual enzyme activity. The activity of the GCase was determined with 3 mM 4-MU-β-Glc in the Reaction Buffer at 37° C. for 1 hr as conduritol B epoxide (CBE)-sensitive activity in parallel assays without or with pre-incubation with CBE at 1.25 mM for 30 min at room temperature. Protein concentrations in the cell lysates were determined using micro BCA protein assay kit from Pierce.

Figure 5:
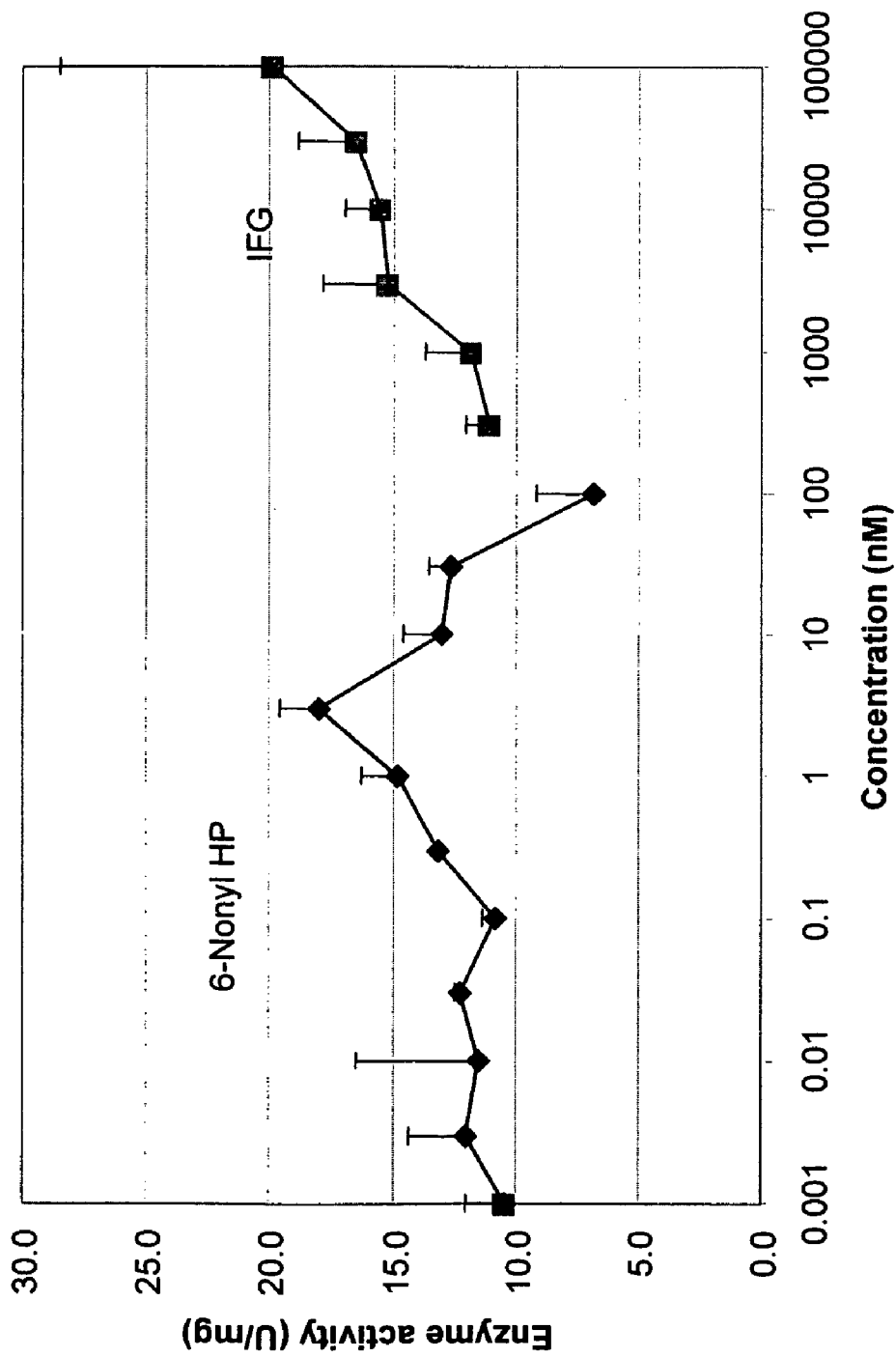
FIG. 5. Chaperone rescue of residual GCase activity in Gaucher fibroblasts. Fibroblasts established from Gaucher patients with N370S/N370S mutation were treated with the compounds of the present invention and the activity of GCase was determined as described in the Examples. Protein concentrations in the cell lysates were also determined using micro BCA protein assay kit from Pierce. ◆=6-nonyl HP; ■=isofagomine (IFG).

Results. In order to examine the ability of the novel compounds to rescue mutant enzyme activity from degradation in the ER, the above-described inhibitors of GCase, 6-nonyl HP and IFG, were added at various concentrations in the culture medium of fibroblasts established from Gaucher patient with homozygous N370S mutation. The residual enzyme activity in patient cells cultivated with inhibitors were shown to be increased approximately 2-fold, although the optimal concentration of each compound varied according to its potency of inhibitory activity (FIG. 5). 6-nonyl HP has the lowest optimal concentration for its chaperone activity at approximate 3 nM, whereas the optimal concentration of IFG was found to be 30 μM. It has been demonstrated that optimal concentration for chaperone activity is dependent on the potency of inhibitory activity and the bioavailability (Fan et al., *Trends Pharmacol Sci.* 2003; 24:355-60). The combination of the highest inhibitory activity and good permeability of C-nonyl HP may contribute the lower optimal concentration as a chaperone for the GCase activity in Gaucher disease.

6-alkyl derivatives of HP with shorter chains, i.e., less than 6 carbons, are not as potent as 6-alkyl derivatives of HP with longer chains, although they maintain a potency comparable to the parent compound, i.e., HP or IFG. These compounds with shorter 6-alkyl chains may be better ASSCs than the parent compound, because they are more lipohydrophilic, which may increase their bioavailibility and bioaccessibility over the parent compound.

What is claimed is:

1. A method of enhancing in a mammalian cell the activity of glucocerebrosidase, comprising contacting the cell with at least one compound in an amount effective to enhance the activity of glucocerebrosidase, wherein the effective amount does not inhibit glucocerebrosidase activity, and wherein the compound is represented by the following formula:

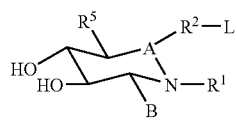

wherein A is a carbon;

B is a hydrogen;

$R^1$ is a hydrogen, substituted or unsubstituted: alkyl;

$R^2$ is an optional C1-C6 alkyl;

$R^5$ is a hydroxymethyl;

L is a 1-12 carbon atom alkyl or benzyl;

$R^2$ and L together have at least 4 carbon atoms;

and pharmaceutically acceptable salts thereof.

2. The method of claim 1, wherein the compound is (3R, 4R, 5R, 6S)-5-(hydroxymethyl)-6-n-butyl-3,4-dihydroxypiperdine.

3. The method of claim 1, wherein the compound is (3R, 4R, 5R, 6S)-5-(hydroxymethyl)-6-n-hexyl-3,4-dihydroxypiperdine.

4. The method of claim 1, wherein the compound is (3R, 4R, 5R, 6S)-5-(hydroxymethyl)-6-n-heptyl-3,4-dihydroxypiperdine.

5. The method of claim 1, wherein the compound is (3R, 4R, 5R, 6S)-5-(hydroxymethyl)-6-n-octyl-3,4-dihydroxypiperdine.

6. The method of claim 1, wherein the compound is (3R, 4R, 5R, 6S)-5-(hydroxymethyl)-6-n-nonyl-3,4-dihydroxypiperdine.

* * * * *

SEQUENCE LISTING

```
<160> NUMBER OF SEQ ID NOS: 2

<210> SEQ ID NO 1
<211> LENGTH: 516
<212> TYPE: PRT
<213> ORGANISM: Homo sapiens

<400> SEQUENCE: 1

Met Ala Gly Ser Leu Thr Gly Leu Leu Leu Leu Gln Ala Val Ser Trp
 1               5                  10                  15

Ala Ser Gly Ala Arg Pro Cys Ile Pro Lys Ser Phe Gly Tyr Ser Ser
                20                  25                  30

Val Val Cys Val Cys Asn Ala Thr Tyr Cys Asp Ser Phe Asp Pro Pro
            35                  40                  45

Thr Phe Pro Ala Leu Gly Thr Phe Ser Arg Tyr Glu Ser Thr Arg Ser
        50                  55                  60

Gly Arg Arg Met Glu Leu Ser Met Gly Pro Ile Gln Ala Asn His Thr
65                  70                  75                  80

Gly Thr Gly Leu Leu Leu Thr Leu Gln Pro Glu Gln Lys Phe Gln Lys
                85                  90                  95

Val Lys Gly Phe Gly Gly Ala Met Thr Asp Ala Ala Ala Leu Asn Ile
            100                 105                 110

Leu Ala Leu Ser Pro Pro Ala Gln Asn Leu Leu Leu Lys Ser Tyr Phe
        115                 120                 125

Ser Glu Glu Gly Ile Gly Tyr Asn Ile Ile Arg Val Pro Met Ala Ser
    130                 135                 140

Cys Asp Phe Ser Ile Arg Thr Tyr Thr Tyr Ala Asp Thr Pro Asp Asp
145                 150                 155                 160
```

```
Phe Gln Leu His Asn Phe Ser Leu Pro Glu Glu Asp Thr Lys Leu Lys
                165                 170                 175

Ile Pro Leu Ile His Arg Ala Leu Gln Leu Ala Gln Arg Pro Val Ser
            180                 185                 190

Leu Leu Ala Ser Pro Trp Thr Ser Pro Thr Trp Leu Lys Thr Asn Gly
        195                 200                 205

Ala Val Asn Gly Lys Gly Ser Leu Lys Gly Gln Pro Gly Asp Ile Tyr
210                 215                 220

His Gln Thr Trp Ala Arg Tyr Phe Val Lys Phe Leu Asp Ala Tyr Ala
225                 230                 235                 240

Glu His Lys Leu Gln Phe Trp Ala Val Thr Ala Glu Asn Glu Pro Ser
                245                 250                 255

Ala Gly Leu Leu Ser Gly Tyr Pro Phe Gln Cys Leu Gly Phe Thr Pro
            260                 265                 270

Glu His Gln Arg Asp Leu Ile Ala Arg Asp Leu Gly Pro Thr Leu Ala
        275                 280                 285

Asn Ser Thr His His Asn Val Arg Leu Leu Met Leu Asp Asp Gln Arg
290                 295                 300

Leu Leu Leu Pro His Trp Ala Lys Val Val Leu Thr Asp Pro Glu Ala
305                 310                 315                 320

Ala Lys Tyr Val His Gly Ile Ala Val His Trp Tyr Leu Asp Phe Leu
                325                 330                 335

Ala Pro Ala Lys Ala Thr Leu Gly Glu Thr His Arg Leu Phe Pro Asn
            340                 345                 350

Thr Met Leu Phe Ala Ser Glu Ala Cys Val Gly Ser Lys Phe Trp Glu
        355                 360                 365

Gln Ser Val Arg Leu Gly Ser Trp Asp Arg Gly Met Gln Tyr Ser His
370                 375                 380

Ser Ile Ile Thr Asn Leu Leu Tyr His Val Val Gly Trp Thr Asp Trp
385                 390                 395                 400

Asn Leu Ala Leu Asn Pro Glu Gly Gly Pro Asn Trp Val Arg Asn Phe
                405                 410                 415

Val Asp Ser Pro Ile Ile Val Asp Ile Thr Lys Asp Thr Phe Tyr Lys
            420                 425                 430

Gln Pro Met Phe Tyr His Leu Gly His Phe Ser Lys Phe Ile Pro Glu
        435                 440                 445

Gly Ser Gln Arg Val Gly Leu Val Ala Ser Gln Lys Asn Asp Leu Asp
450                 455                 460

Ala Val Ala Leu Met His Pro Asp Gly Ser Ala Val Val Val Val Leu
465                 470                 475                 480

Asn Arg Ser Ser Lys Asp Val Pro Leu Thr Ile Lys Asp Pro Ala Val
                485                 490                 495

Gly Phe Leu Glu Thr Ile Ser Pro Gly Tyr Ser Ile His Thr Tyr Leu
            500                 505                 510

Trp Arg Arg Gln
515

<210> SEQ ID NO 2
<211> LENGTH: 1792
<212> TYPE: DNA
<213> ORGANISM: Homo sapiens

<400> SEQUENCE: 2
ccttccagag aggaatgtcc caagcctttg agtagggtaa gcatcatggc tggcagcctc    60
```

-continued

```
acaggattgc ttctacttca ggcagtgtcg tgggcatcag gtgcccgccc ctgcatccct    120
aaaagcttcg gctacagctc ggtggtgtgt gtctgcaatg ccacatactg tgactccttt    180
gacccccga  cctttcctgc ccttggtacc ttcagccgct atgagagtac acgcagtggg    240
cgacggatgg agctgagtat ggggcccatc caggctaatc acacgggcac aggcctgcta    300
ctgaccctgc agccagaaca gaagttccag aaagtgaagg gatttggagg gccatgaca     360
gatgctgctg ctctcaacat ccttgccctg tcaccccctg cccaaaattt gctacttaaa    420
tcgtacttct ctgaagaagg aatcggatat aacatcatcc gggtacccat ggccagctgt    480
gacttctcca tccgcaccta cacctatgca gacacccctg atgatttcca gttgcacaac    540
ttcagcctcc cagaggaaga taccaagctc aagataccc  tgattcaccg agcactgcag    600
ttggcccagc gtcccgtttc actccttgcc agccctgga  catcacccac ttggctcaag    660
accaatggag cggtgaatgg gaaggggtca ctcaagggac agcccggaga catctaccac    720
cagacctggg ccagatactt tgtgaagttc ctggatgcct atgctgagca caagttacag    780
ttctgggcag tgacagctga aaatgagcct tctgctgggc tgttgagtgg atacccttc     840
cagtgcctgg gcttcaccc  tgaacatcag cgagacttaa ttgcccgtga cctaggtcct    900
accctcgcca acagtactca ccacaatgtc cgcctactca tgctggatga ccaacgcttg    960
ctgctgcccc actgggcaaa ggtggtactg acagacccag aagcagctaa atatgttcat   1020
ggcattgctg tacattggta cctggacttt ctggctccag ccaaagccac cctaggggag   1080
acacaccgcc tgttccccaa caccatgctc tttgcctcag aggcctgtgt gggctccaag   1140
ttctgggagc agagtgtgcg gctaggctcc tgggatcgag ggatgcagta cagccacagc   1200
atcatcacga acctcctgta ccatgtggtc ggctggaccg actggaacct tgccctgaac   1260
cccgaaggag gacccaattg ggtgcgtaac tttgtcgaca gtcccatcat tgtagacatc   1320
accaaggaca cgttttacaa acagcccatg ttctaccacc ttggccattt cagcaagttc   1380
attcctgagg gctcccagag agtggggctg gttgccagtc agaagaacga cctggacgca   1440
gtggcattga tgcatcccga tggctctgct gttgtggtcg tgctaaaccg ctcctctaag   1500
gatgtgcctc ttaccatcaa ggatcctgct gtgggcttcc tggagacaat ctcacctggc   1560
tactccattc acacctacct gtggcgtcgc cagtgatgga gcagatactc aaggaggcac   1620
tgggctcagc ctgggcatta aagggacaga gtcagctcac acgctgtctg tgactaaaga   1680
gggcacagca gggccagtgt gagcttacag cgacgtaagc ccaggggcaa tggtttgggt   1740
gactcacttt ccctctagg  tggtgccagg ggctggaggc ccctagaaaa ag           1792
```